United States Patent
Haschemi et al.

(10) Patent No.: US 10,130,117 B2
(45) Date of Patent: *Nov. 20, 2018

(54) USE OF SEDOHEPTULOSE AS A NUTRITIONAL SUPPLEMENT

(71) Applicant: C7 SUGAR GMBH, Vienna (AT)

(72) Inventors: Arvand Haschemi, Vienna (AT); Oswald Wagner, Vienna (AT); Csorsz Nagy, Vienna (AT); Rodrig Marculescu, Altenberg (AT)

(73) Assignee: C7 SUGAR GMBH, Vienna (AT)

(*) Notice: Subject to any disclaimer, the term of this patent is extended or adjusted under 35 U.S.C. 154(b) by 0 days.

This patent is subject to a terminal disclaimer.

(21) Appl. No.: 15/601,116

(22) Filed: May 22, 2017

(65) Prior Publication Data

US 2017/0303577 A1 Oct. 26, 2017

Related U.S. Application Data

(63) Continuation of application No. 14/778,898, filed as application No. PCT/EP2014/055673 on Mar. 21, 2014, now Pat. No. 9,675,099.

(30) Foreign Application Priority Data

Mar. 21, 2013 (EP) .................................. 13160426

(51) Int. Cl.
*A23L 1/29* (2006.01)
*A23L 33/20* (2016.01)
*A61K 31/7004* (2006.01)
*A23L 2/60* (2006.01)
*A23L 27/30* (2016.01)

(52) U.S. Cl.
CPC ................. *A23L 33/20* (2016.08); *A23L 2/60* (2013.01); *A23L 27/33* (2016.08); *A61K 31/7004* (2013.01); *A23V 2002/00* (2013.01)

(58) Field of Classification Search
CPC . A23L 33/20; A23L 27/33; A23L 2/60; A61K 31/7004
USPC .............................................. 426/2, 648, 658
See application file for complete search history.

(56) References Cited

U.S. PATENT DOCUMENTS

| | | | |
|---|---|---|---|
| 2007/0098818 A1 | 5/2007 | Smith | 424/680 |
| 2009/0252834 A1 | 10/2009 | Hayek et al. | 426/66 |
| 2011/0123670 A1 | 5/2011 | Tanner et al. | 426/2 |
| 2015/0282513 A1 | 10/2015 | Cook et al. | 514/777 |
| 2016/0045525 A1 | 2/2016 | Haschemi et al. | 514/23 |

FOREIGN PATENT DOCUMENTS

| | | |
|---|---|---|
| EP | 0221728 | 5/1987 |
| JP | H04-335877 | 11/1992 |
| JP | 2007137797 | 6/2007 |
| WO | WO 2006/027796 | 3/2006 |

(Continued)

OTHER PUBLICATIONS

Adams et al. "A Diet Rich in Green and Yellow Vegetables Inhibits Atherosclerosis in Mice," *The Journal of Nutrition*, 2006; 136(7): 1886-9.

(Continued)

Primary Examiner — Helen F Heggestad
(74) Attorney, Agent, or Firm — Norton Rose Fulbright US LLP

(57) ABSTRACT

The invention discloses the use of sedoheptulose as a nutritional supplement.

11 Claims, 12 Drawing Sheets

(56) References Cited

FOREIGN PATENT DOCUMENTS

| WO | WO 2006/093848 | 9/2006 |
|---|---|---|
| WO | WO 2009/066822 | 5/2009 |

OTHER PUBLICATIONS

Haschemi, A. et al. "The sedoheptulose kinase CARKL directs macrophage polarization through control of glucose metabolism," *Cell Metabolism*, vol. 15 (2015), 813-826.

Hernandez-Hernandez, O. et al. "Determination of free inositols and other low molecular weight carbohydrates in vegetables," *Journal of Agricultural and Food Chemistry*, vol. 59, (2011), 2451-2455.

Herrman, J.L. et al. "Hepatic carbamyl phosphate: glucose phosphotransferase. Distribution, comparative kinetics, and responses to alloxan- or mannoheptulose-induced diabetes," *Archives of Biochemistry and Biophysics*, vol. 152 (1972), 180-186.

Jiang, P et al "p53 regulates biosynthesis through direct inactivation of glucose-6-phosphate dehydrogenase," *Nat. Cell Biol.* vol. 13(3), (2011), 310-316.

Kardon et al. "Characterization of mammalian sedoheptulokinase and mechanism of formation of erythritol in sedoheptulokinase deficiency," *FEBS Letters* 582 (2008) 3330-3334.

Lindroos, J et al "Human but not mouse adipogenesis is critically dependent on LMO3," *Cell Metabolism*, vol. 18 (2013), 62-74.

Nagy, C. et al. "Sedoheptulose kinase regulates cellular carbohydrate metabolism by sedoheptulose 7-phosphate supply," *Biochemical Society Transactions*, vol. 41, (2013), 674-680.

Patel, C.J. et al. "Systematic identification of interaction effects between genome- and environment-wide associations in type 2 diabetes mellitus," *Hum. Genet*, vol. 132, (2013), 495-508.

Ruiz-Matute, A.I. et al. "Derivatization of carbohydrates for GC and GC-MS analyses," *Journal of Chromatography B*, 879, (2011), 1226-1240.

Schillinger, M. et al. "Inflammation and Carotid Artery—Risk for Atherosclerosis Study (ICARAS)," *Circulation*, vol. 111, (2005), 2203-2209.

Soria, A.C. et al "Determination of minor carbohydrates in carrot (*Daucus carota* L.) by GC-MS," *Food Chemistry*, vol. 114 (2009), 758-762.

Zuo, CN 101919872, Dec. 22, 2010, machine translation.

Noh et al., "7-O-Galloyl-D-sedoheptulose Attenuates Oxidative Stress-Induced Diabetic Injury via Decreasing Expression of Nuclear Factor-κB- and Apoptosis-Related Protein in the Liver," *Biol. Pharm. Bull.*, 2012, 35(6): 950-956.

Agawa, "Effect of Disaccharides, Heptose and Sialic Acid on Release of Glucagon From the Isolated Perfused Rat Pancreas", *Chemical Abstracts*, 26(4). (1984).

Office Action Issued in Corresponding European Patent Application No. 14711752.7, dated Jan. 29, 2018.

Garcia-Leme, et al., "Hormonal Control of Inflammatory Responses." *Mediators of Inflammation*, 2(3), pp. 181-198, 1993.

Sirianni, et al., "Modulation of Human Natural Killer Activity by Vasoactive Intestinal Peptide (VIP) Family. VIP, Glucagon and GHRF Specifically Inhibit NK Activity." *Regulatory Peptides, Elsevier Science BV, NL*, 38, pp. 79-87, 1992.

Office Action issued in European Application No. 14711754.3, dated Jan. 29, 2018.

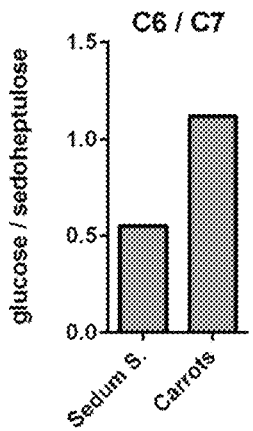
FIG. 1A
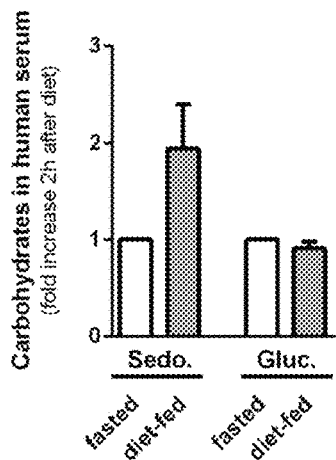
FIG. 1B
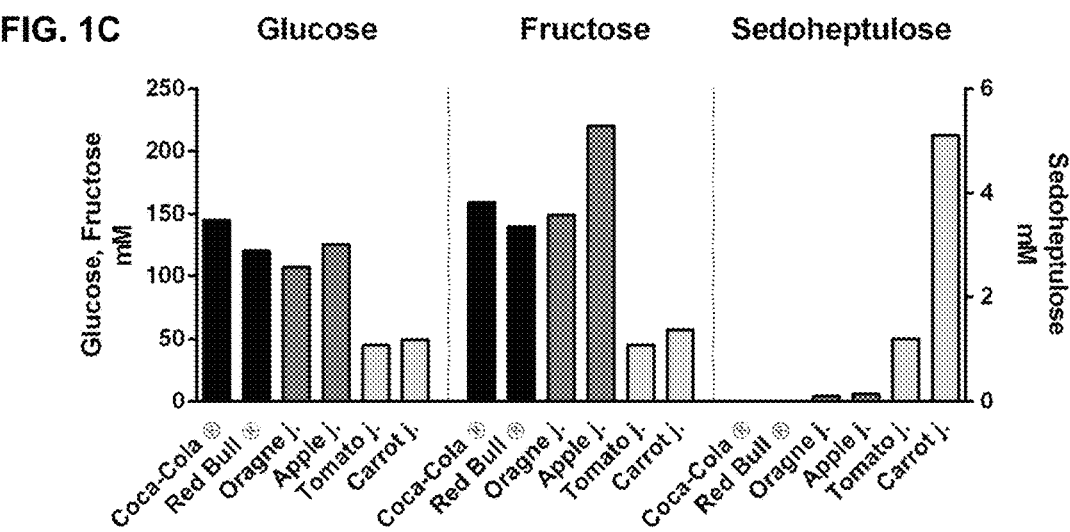
FIG. 1C
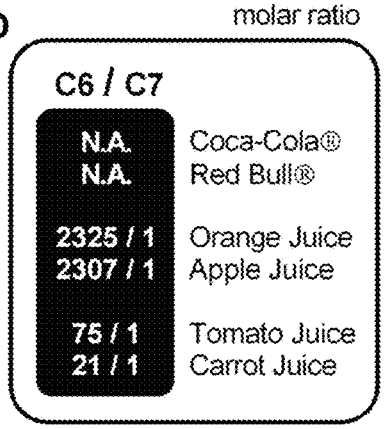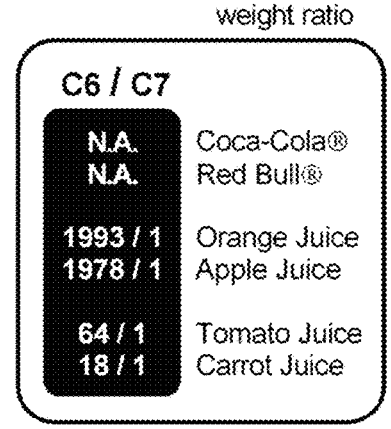
FIG. 1D

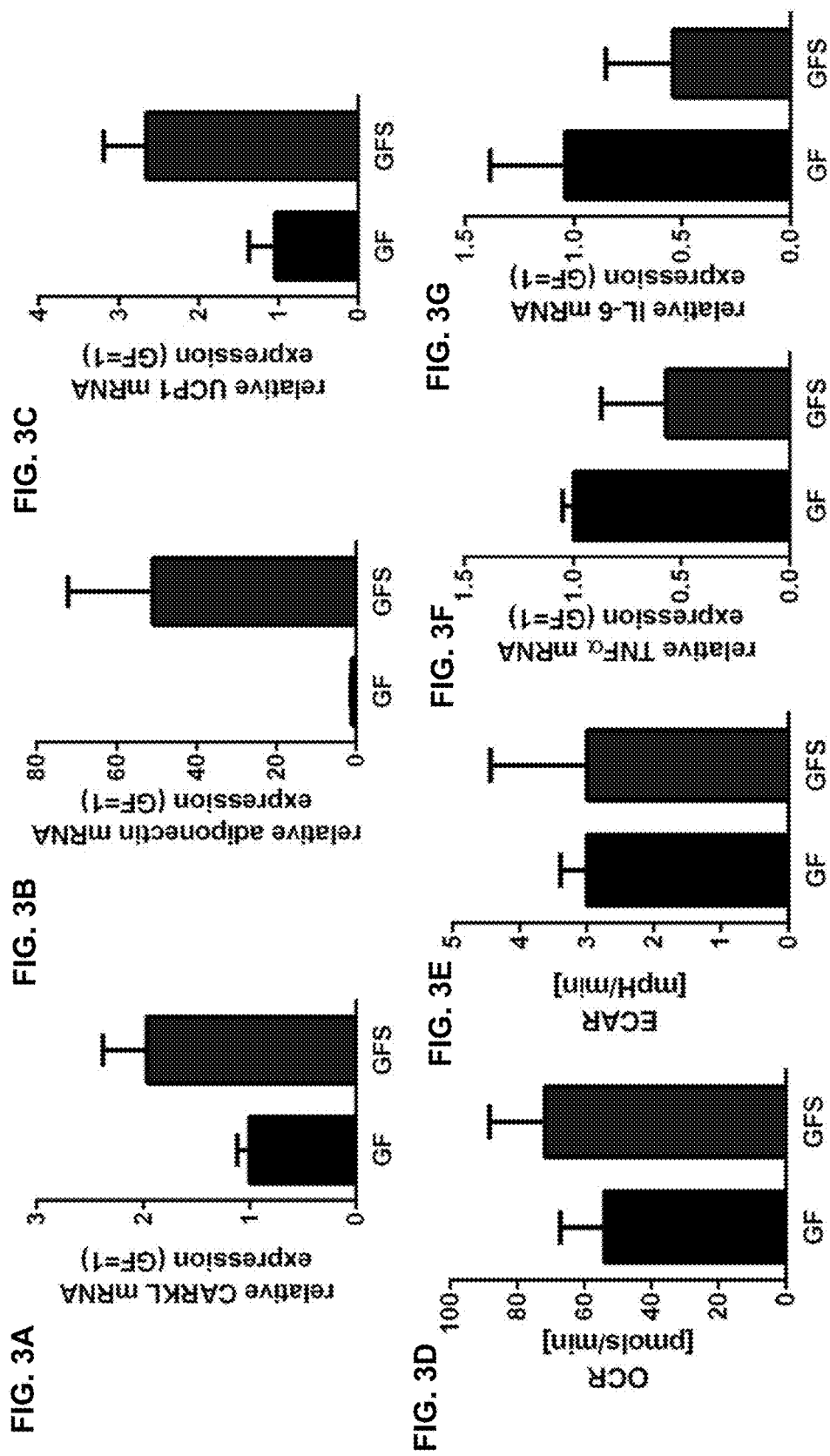

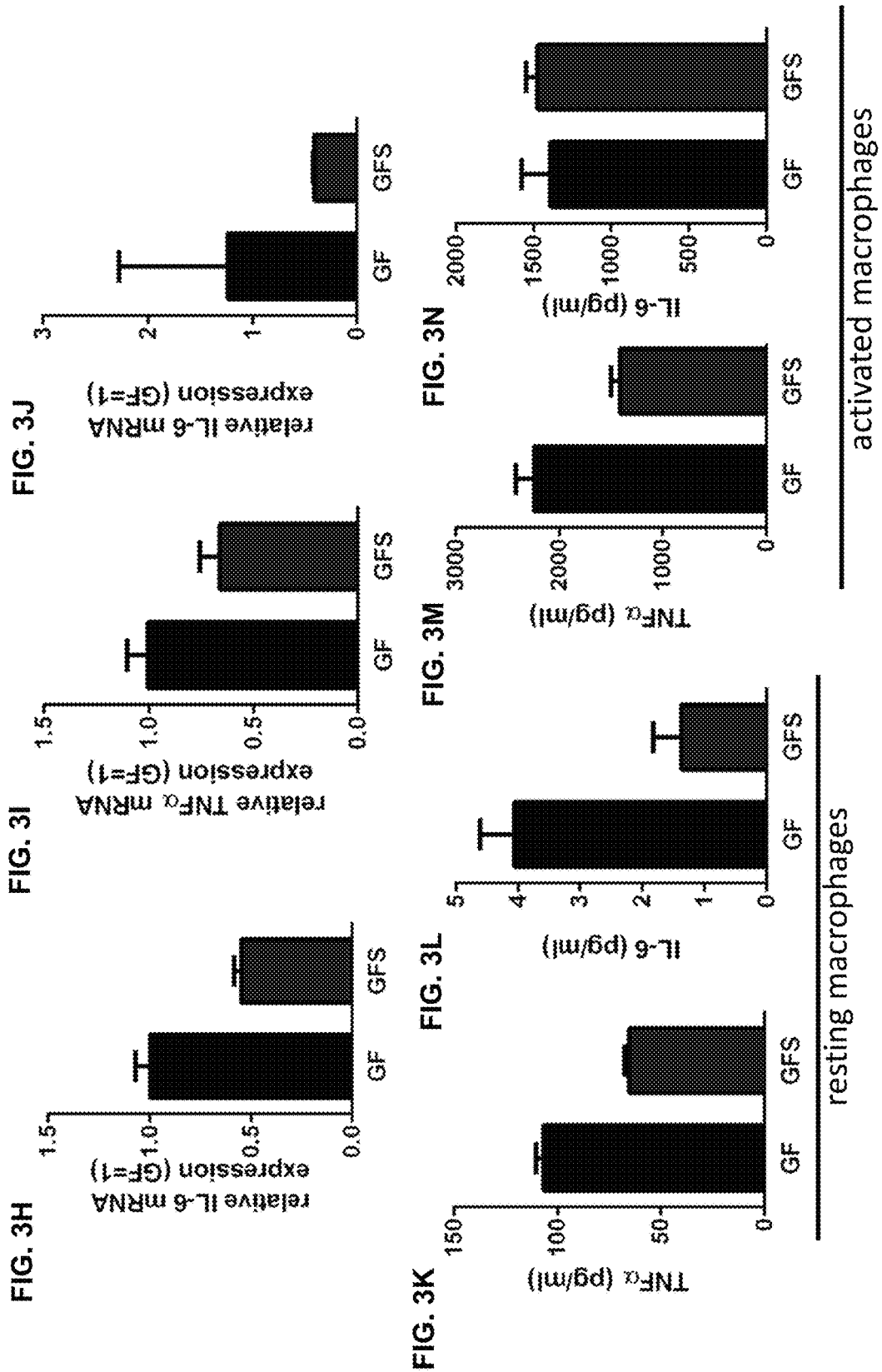

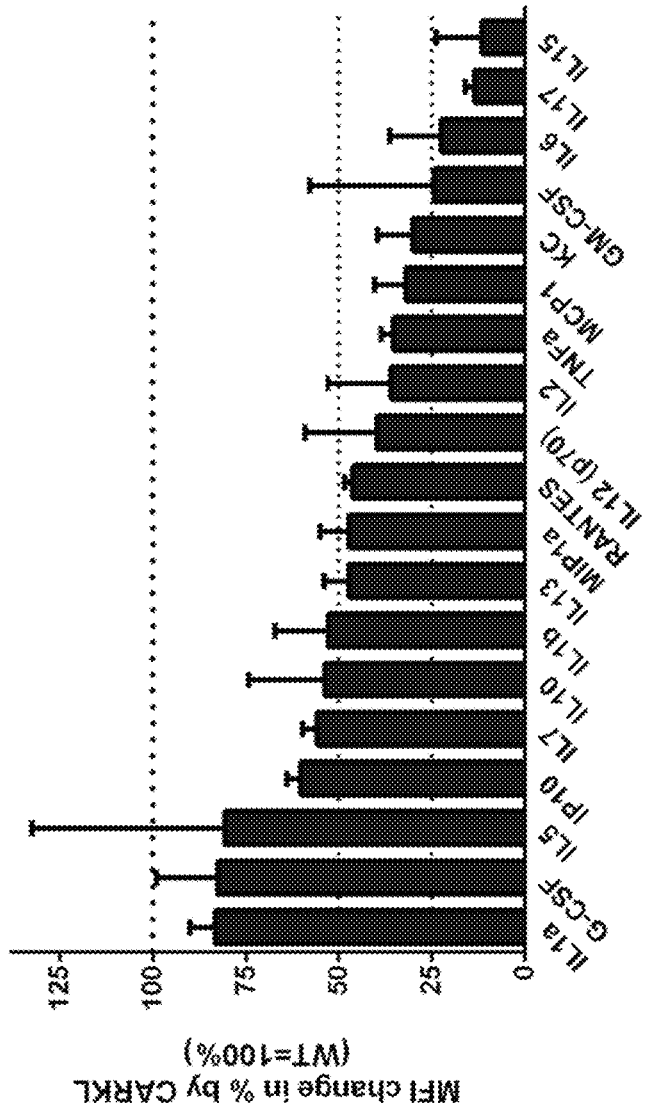
FIG. 6A
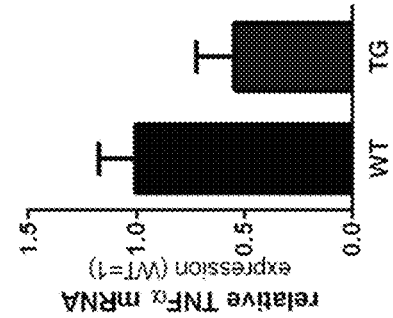
FIG. 6B
FIG. 6C
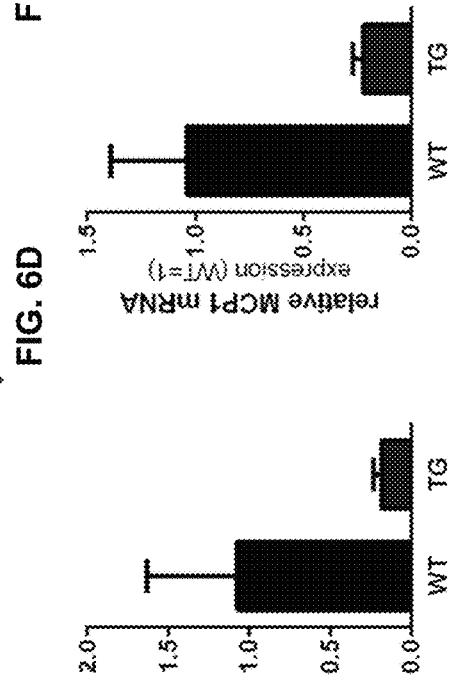
FIG. 6D
FIG. 6E
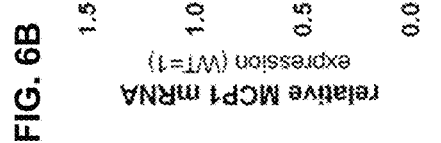

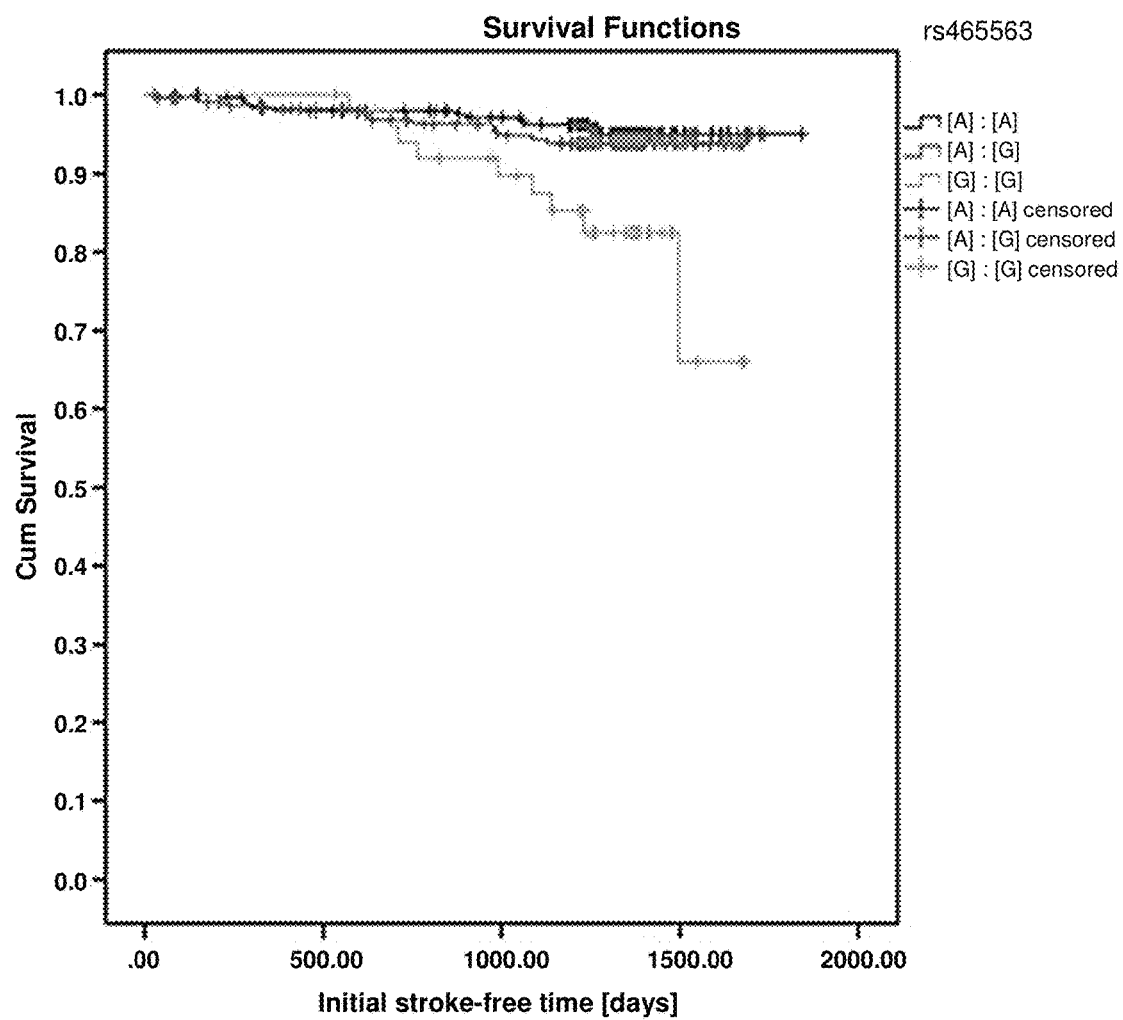

USE OF SEDOHEPTULOSE AS A NUTRITIONAL SUPPLEMENT

CROSS-REFERENCE TO RELATED APPLICATIONS

This application is a continuation of U.S. patent application Ser. No. 14/778,898, which is a national phase application under 35 U.S.C. § 371 of International Application No. PCT/EP2014/055673 filed 21 Mar. 2014, which claims priority to European Patent Application No. 13160426.6 filed 21 Mar. 2013. The entire contents of each of the above-referenced disclosures is specifically incorporated herein by reference without disclaimer.

BACKGROUND OF THE INVENTION

1. Field of the Invention

The present invention relates to the field of nutritional supplementation.

2. Description of Related Art

A nutritional supplement, also known as food supplement or dietary supplement, is a preparation intended to supplement the diet and provide nutrients, such as vitamins, minerals, fiber, fatty acids, or amino acids that may be missing or may not be consumed in sufficient quantities in a person's diet. Some countries define dietary supplements as foods, while in others they are defined as drugs or natural health products.

Supplements containing vitamins or dietary minerals are included as a category of food in the Codex Alimentarius, a collection of internationally recognized standards, codes of practice, guidelines and other recommendations relating to foods, food production and food safety. These texts are drawn up by the Codex Alimentarius Commission, an organization that is sponsored by the Food and Agriculture Organization (FAO) of the United Nations and the World Health Organization (WHO).

The average American consumes an astounding 1 to 1.5 kg of sugar (mainly as glucose) each week, which is not surprising considering that highly refined sugars in the forms of sucrose (table sugar), dextrose (corn sugar), and high-fructose corn syrup are being processed into so many foods such as bread, breakfast cereal, mayonnaise, peanut butter, ketchup, spaghetti sauce, and a plethora of microwave meals and beverages.

One of sugar's major drawbacks is that it raises the insulin level, which inhibits the release of growth hormones, which in turn depresses the immune system. An influx of sugar into the bloodstream upsets the body's blood-sugar balance, triggering the release of insulin, which the body uses to keep blood-sugar at a constant and safe level. Insulin also promotes the storage of fat, so that when you eat sweets high in sugar, you are making way for rapid weight gain and elevated triglyceride levels, both of which have been linked to cardiovascular disease. Complex carbohydrates tend to be absorbed more slowly, lessening the impact on blood-sugar levels.

The health dangers which ingesting sugar on a habitual basis creates are certain. Simple sugars, especially glucose, have been observed to aggravate asthma, move mood swings, provoke personality changes, muster mental illness, nourish nervous disorders, deliver diabetes, hurry heart disease, grow gallstones, hasten hypertension, and add arthritis.

The glycemic index, or glycaemic index, (GI) provides a measure of how quickly blood sugar levels (i.e. levels of glucose in the blood) rise after eating a particular type of food. The effects that different foods have on blood sugar levels vary considerably. The glycemic index estimates how much each gram of available carbohydrate (total carbohydrate minus fiber) in a food raises a person's blood glucose level following consumption of the food, relative to consumption of pure glucose. Glucose has a glycemic index of 100. A practical limitation of the glycemic index is that it does not take into account the amount of carbohydrate actually consumed. A related measure, the glycemic load, factors this in by multiplying the glycemic index of the food in question by the carbohydrate content of the actual serving.

A low-GI food will release glucose more slowly and steadily, which leads to more suitable postprandial (after meal) blood glucose readings. A high-GI food causes a more rapid rise in blood glucose levels and is suitable for energy recovery after exercise or for a person experiencing hypoglycemia.

The glycemic effect of foods depends on a number of factors such as the type of starch (amylose versus amylopectin), physical entrapment of the starch molecules within the food, fat and protein content of the food and organic acids or their salts in the meal—adding vinegar, for example, will lower the GI. The presence of fat or soluble dietary fiber can slow the gastric emptying rate, thus lowering the GI. In general, coarse, grainy breads with higher amounts of fiber have a lower GI value than white breads. However, most breads made with 100% wholewheat or wholemeal flour have a GI not a whole lot different than endosperm only (white) bread. Many brown breads are treated with enzymes to soften the crust, which makes the starch more accessible (high GI).

While adding fat or protein will lower the glycemic response to a meal, the relative differences remain. That is, with or without additions, there is still a higher blood glucose curve after a high GI bread than after a low-GI bread such as pumpernickel. Fruits and vegetables tend to have a low glycemic index. The glycemic index can be applied only to foods where the test relies on subjects consuming an amount of food containing 50 g of available carbohydrate. But many fruits and vegetables (not potatoes, sweet potatoes, corn) contain less than 50 g of available carbohydrate per typical serving. Carrots were originally and incorrectly reported as having a high GI. Alcoholic beverages have been reported to have low GI values, but it should be noted that beer has a moderate GI. Recent studies have shown that the consumption of an alcoholic drink prior to a meal reduces the GI of the meal by approximately 15%. Moderate alcohol consumption more than 12 hours prior to a test does not affect the GI.

Many modern diets rely on the glycemic index. However, others have pointed out that foods generally considered to be unhealthy can have a low glycemic index, for instance, chocolate cake, ice cream, or pure fructose, whereas foods like potatoes and rice, eaten in countries with low rates of diabetes, have GIs around 100.

SUMMARY OF THE INVENTION

It is an object of the present invention to provide nutritional supplements that improve energy metabolism of the food in humans. It is a further object to provide an alternative food classification index for the GI that takes into account the effect of the food product on metabolism.

Therefore, the present invention provides the use of sedoheptulose as a nutritional inducer of cellular oxygen consumption. The present invention also provides the use of sedoheptulose, a nutritional inhibitor of extracellular acidification, glycolysis and lactate formation. The present invention also provides the use of sedoheptulose for reducing glycaemic load in food products. The present invention also provides the use of sedoheptulose as a nutritional supplement, especially for safeguarding a lack of sedoheptulose deficiency in healthy individuals, i.e. providing sedoheptulose without therapeutic need or background.

The present invention makes use of the fact that free sedoheptulose is a relevant and accessible carbon source in humans. Furthermore, the bio-availability of its phosphorylated form, sedoheptulose-7-phosphate, appears to function as a rheostat for hexose carbohydrate metabolism at the interface of glycolysis and the pentose phosphate pathway as well as for mitochondrial respiration. Nutritional sedoheptulose appears to balance cellular glucose consumption, fat combustion, redox regulation, inflammation and therefore related disorders.

It is shown with the present invention that distinctive nutritional value is provided by the addition of sedoheptulose to food products compared to all presently used carbohydrates, including commonly used non-caloric and caloric sweeteners. The present invention is therefore directed to balance C6 (over)consumption, thereby preventing obesity or diabetes and optimising and strengthening immune function and energy utilisation. Accordingly, the "nutritional" supplement according to the present invention is used in the meaning of "providing or improving nutrient utilisation" by the addition of sedoheptulose to food products and thereby providing new and improved food products with a sedoheptulose content (or by improving food products by (further) increasing sedoheptulose content). The C7 nutritional supplement according to the present invention therefore provides an effective strategy to manage physiological redox-regulation and thereby also manage related metabolic disturbances or disorders. Accordingly, the present invention significantly differs from the reduced calorie sweeter or brown sugar substitute use suggested in WO 2006/027796 A2 and WO 2006/093848 A2.

As already stated, today's food industry uses high quantities of C6 sugars (C6 sugars are glucose, fructose and sucrose and maltose (as respective dimers thereof)) as nutritional supplements. Most of these hexoses are used as a sweetener (i.e. not as a "nutritional" supplement, but as a taste or flavour enhancer) and are widely discussed to increase the risk of cardiovascular diseases, Alzheimer's disease, metabolic-syndrome, obesity and diabetes. The ratio of C6 to C7 carbohydrates is disturbed by excessive C6 application. Addition of C7 (i.e. mainly sedoheptulose, however, also combinations with other C7 sugars is possible, especially mannoheptulose; besides sedoheptulose alone, C7 can be defined as "sedoheptulose with or without mannoheptulose in a sedo/manno % w/w ratio of at least 10.000:1, preferably at least 1.000:1 and especially at least 100:1") will balance increased glycaemic-loads. C7 is not as sweet as C6 and does thereby not significantly alter taste of supplemented foods. C7 carbohydrates have a distinct function in cellular carbohydrate and fat metabolism and thereby impact nutrition as well as healthcare related aspects in vertebrates.

Accordingly, the present invention provides the teaching that addition of C7 to diets results in improved and balanced metabolism in human and mice. The nutritional supplement containing C7 according to the present invention has the clear potential to alter the preference for C6 sweetened food products in respect to health-care related issues.

With the present invention also a new parameter for nutritional effectiveness is provided, the C6/C7 ratio that is provided and made available for natural and chemically-designed standard diets as well as natural and chemically-designed food ingredients. With the present invention it could also be demonstrated that C7 consumption manages energy efficiency, manages tissue health and inflammation. Moreover, C7 consumption induced and provided by the present invention also manages physical endurance, physiological redox-regulation and thereby also related disorders, such as diabetes and obesity.

Sedoheptulose (CAS number: 3019-74-7; PubChem: 5459879; ChemSpider: 4573620; MeSH: sedoheptulose; ChEBI: CHEBI:16802) or D-altro-heptulose is a ketoheptose—a monosaccharide with seven carbon atoms and a ketone functional group. It is one of the few heptoses found in nature. Sedoheptulose is producible by extraction from natural sources or by chemical synthesis. It can be purified to high purity degrees (e.g. >60% purity, preferably >85% purity, more preferred >90% purity, more preferred >95% purity, even more preferred >99% purity, especially >99.9% purity).

Sedoheptulose is a relatively unknown metabolite compared to its phosphorylated form, sedoheptulose-7-phosphate (S7P), which is recognised as an intermediate molecule of primary glucose metabolism. The natural existence of sedoheptulose, was first reported in plants and was subsequently identified in human urine, blood spots and recently, within mouse cells. S7P is derived from the transketolase-catalysed conversion of ribose-5-phosphate (R5P) and xylulose-5-phosphate (X5P). This reaction occurs in the non-oxidative arm of the pentose phosphate pathway and generates glyceraldehyde-3-phosphate (G3P), a key glycolytic intermediate, in addition to S7P. G3P and S7P are also produced by transaldolase using fructose-6-phosphate (F6P) and erythrose-4-phosphate (E4P) as substrates. S7P is thus a crucial intermediate in the non-oxidative PPP and S7P bioavailability therefore contributes to cellular carbon flux. Recently, data from several groups have indicated that sedoheptulose kinase may also produce S7P by direct phosphorylation of sedoheptulose (Haschemi et al., Cell Metab. 15 (2012), 813-826). This finding demonstrated the unexpected existence of an additional carbon source, sedoheptulose, which actively participates in cellular carbon metabolism (Nagy and Haschemi, Biochem Soc Trans. 2013).

Free sedoheptulose can either be diet-derived from fruits and vegetables or formed enzymatically by the dephosphorylation of endogenously produced S7P. Thus far, no specific sedoheptulose transporter or S7P-specific phosphatase has been reported. Other bio-active heptoses include the phenolic compound 7-O-Galloyl-sedoheptulose (GS), mannoheptulose and glucoheptose. GS was reported to be protective in diabetic injury of the kidney by alleviating inflammatory responses. Mannoheptulose (various patents pending) is an isomer of sedoheptulose and a potent hexokinase inhibitor commonly found in avocados. Glucoheptose, although the chemical nature of this compound remains unidentified, has been shown to serve as accessible carbohydrate source in rabbits. Sedoheptulosan is the anhydride of sedoheptulose and might also serve as source for free sedoheptulose.

Free sedoheptulose can be isolated, e.g. from the plant *sedum spectabile* and has been previously reported to contain high amounts of heptose-carbohydrates.

Sedoheptulose kinase phosphorylates free sedoheptulose, which enables cells to directly route sedoheptulose to carbohydrate metabolism, similar to hexokinase and glucose. According to the present invention, sedoheptulose is a direct carbon source that feeds primary carbohydrate catabolism and anabolism, whereupon sedoheptulose kinase (CARKL) constitutes its entry point. Sedoheptulose can therefore surprisingly be compared to glucose and fructose because these compounds all exist as free carbohydrates and phosphorylated forms. To enter metabolism, free carbohydrates are energetically activated by an initial phosphorylation event. Hexokinase phosphorylates glucose to form G6P and is a key determinant of cellular glucose flux. Fructose is phosphorylated by ketohexokinase to form fructose-1-phosphate (F1P), which must first be converted by aldolase to glyceraldehyde and dihydroxyacetone phosphate (DHAP). DHAP can then directly enter the carbon-cycle, whereas glyceraldehyde must be further phosphorylated. The formation of S7P from sedoheptulose by sedoheptulose kinase, in a manner analogous to G6P formation from glucose by hexokinase, enables free sedoheptulose to readily enter the catabolic system. It was also reported that a competitive inhibition of F6P phosphorylation takes place in the presence of high S7P concentrations. Interestingly, fractions containing fructose 1,6-bisphosphatase (FBPase) were also reported to possess sedoheptulose 1,7-bisphosphatase (SB-Pase) activity.

The present invention therefore is also based on a co-existence of the hexose- and heptose-(bis)phosphate shunts. Notably, high glucose levels or incubation with F2,6bP augmented the S1,7bP formation in perfused rat liver and in rat liver cytosol, respectively. Glucagon, in contrast to high glucose, favoured S1,7bP dephosphorylation and therefore S7P formation. These results show that sedoheptulose metabolism is sensitive to hormonal control.

Sedoheptulose metabolism participates in metabolic regulation; in fact, sedoheptulose directs metabolic fluxes by providing an S7P supply independently from glucose. Increased CARKL expression (and therefore increased sedoheptulose consumption) in a mouse macrophage cell line resulted in reduced G3P, X5P and R5P steady state levels, whereas CARKL knockdown showed the reverse effect. Notably, the basal sedoheptulose levels were not changed by CARKL perturbation. The S7P levels were not changed by overexpression but decreased significantly by CARKL loss, indicating sedoheptulose phosphorylation as a rate-limiting factor for glycolysis-derived G3P distribution. Therefore, the regulation of S7P availability might be the mechanism by which CARKL or excessive amounts of sedoheptulose modulate cellular metabolism.

The present invention is therefore directed to use of C7 e.g. to balance C6-(over)consumption, obesity, diabetes, immune function and—generally—vertebrate's energy utilization. The C7 supplement therefore also provides an effective strategy to manage physiological redox-regulation and thereby also related disorders. With the present invention, it turned out that, both, high sedoheptulose and high sedoheptulose kinase results in enhanced sedoheptulose turn-over. Moreover, tissue expression of sedoheptulose kinase reveals that metabolic organs such as liver or adipose-tissue have the capability to consume sedoheptulose. Additionally, brown-adipose tissue (burns high amounts of lipids) express significantly more (~2.5 x) sedoheptulose kinase than white-adipose tissue.

Sedoheptulose (and/or other heptoses), administered to patients having inflammation or being at risk of suffering from inflammation, minimizes the glycemic-load and positively contributes to prevent e.g. diet-induced obesity and/or diabetes. Furthermore, data from transgenic sedoheptulose kinase animals—as model for enhanced sedoheptulose metabolism—show that high sedoheptulose metabolism increases lipid-oxidation (indicated by lower RQ values). This is a beneficial effect of enhanced sedoheptulose turn-over. Also energy expenditure is lower in animals with high sedoheptulose turnover. Furthermore, it appears that CARKL overexpressing mice are more insulin sensitive than control animals. Taken together, this again shows that sedoheptulose metabolism is an effective mean to regulate the metabolic-phenotype in vertebrates.

With the present invention, specific and surprising anti-inflammatory effects could be shown to be caused by high sedoheptulose turnover: Enhanced inflammation plays an important role in the development of diseases, such as obesity related disorders like insulin resistance. In a functional kinase screen for novel regulators of macrophages activation, sedoheptulose kinase was found to repress the lipopolysaccharide (LPS) induced tumour necrosis factor α secretion. In the same screen, overexpression of hexokinase, ketohexokinase and phosphofructokinase (high glucose/fructose metabolism) had the opposite effect. This showed opposite effects of hexose and heptose-carbohydrate metabolism: heptose inhibit inflammation. Moreover, increased CARKL expression repressed LPS-induced macrophage activation and resulted in blunted intracellular superoxide formation, whereas loss of CARKL (mimics reduced sedoheptulose metabolism) enhanced the inflammatory response of those cells.

On the other hand, the present invention also relates to the prevention of all kind of sedoheptulose deficits, especially those that have not yet lead to pathological consequences, i.e. to counteract a sedoheptulose deficit so that disorders that are due to such sedoheptulose deficits can be prevented. In order to prevent such sedoheptulose deficits, a sedoheptulose containing composition can be administered to an individual being at risk of developing such sedoheptulose deficit (or sedoheptulose deficit syndrome), or a healthy individual without such risk, e.g. as nutritional supplement or in combination with food and/or beverages.

According to a preferred embodiment of the present invention, sedoheptulose is added to a food product already containing sedoheptulose and to obtain a sedoheptulose content of the food product that is increased at least 10%, preferably to obtain a sedoheptulose content of the food product that is increased at least 100%, especially at least 500%.

Alternatively, if sedoheptulose is added to a food product not already containing sedoheptulose, preferably a sedoheptulose content of the food product is obtained that is at least 0.001% w/w, preferably at least 0.01% w/w, more preferred at least 0.1% w/w, even more preferred at least 1% w/w, especially at least 10% w/w.

If the food product is a liquid food product, such as a beverage (e.g. a soft drink), the sedoheptulose content can also be referred to as a % w/v ratio. Accordingly, the present invention also has as preferred embodiments beverages with a sedoheptulose content of at least 0.001% w/v, preferably at least 0.01% w/v, more preferred at least 0.1% w/v, even more preferred at least 1% w/v, especially at least 10% w/v. A "weight ratio" as referred to below therefore means for a liquid food product the % w/w as well as the % w/v value.

For example, for usual soft drinks which are not based on natural fruit (or vegetable) material (juices), only a minimal addition of sedoheptulose is necessary to improve the sedoheptulose content. For the purpose of the present invention "soft drinks" are beverages that typically contain water (often, but not always, carbonated water), usually a sweetener and usually a flavouring agent, but with no fruit juice (these are referred to as "fruit juices within the present invention and a clear difference is maintained for the purpose of the present invention). The sweetener in soft drinks may be sugar, high-fructose corn syrup, fruit juice, sugar substitutes (in the case of diet drinks) or some combination of these. Soft drinks may also contain caffeine, colourings, preservatives and other ingredients. Since soft drinks (as defined according to the present invention) do not contain sedoheptulose (i.e. have a sedoheptulose content well below 0.001% w/w or % w/v), a preferred embodiment of the present invention is a soft drink that has a sedoheptulose content of 0.001% w/w (or % w/v) or above, preferably at least 0.01% w/w (or % w/v), more preferred at least 0.1% w/w (or % w/v), even more preferred at least 1% w/w (or % w/v), especially at least 10% w/w (or % w/v).

According to the present invention, a food product can be analysed with respect to its content in % w/w, % w/v or molar concentration of C6-carbohydrates, especially glucose, fructose and sucrose and maltose as respective dimers, and with respect to its content in % w/w, % w/v or molar concentration of C7-carbohydrates, especially sedoheptulose and, optionally, mannoheptulose, establishing the ratio of C6-carbohydrates to C7-carbohydrates (in % w/w: % w/w, % w/v: % w/v or molar ratio) for this food product, and wherein sedoheptulose with or without mannoheptulose is added to the food product in an amount to decrease the ratio of C6-carbohydrates to C7-carbohydrates (in % w/w: % w/w, % w/v:% w/v or molar ratio) by at least 50%, preferably by at least 100%, especially by at least 200%. Preferably, the weight ratio (i.e. the % w/w and/or the % w/v) in the food product is decreased to a resulting C6/C7 weight ratio of or below 2000%:1%, preferably to a resulting C6/C7 weight ratio of or below 100%:1%, more preferred to a resulting C6/C7 weight ratio of or below 10:1, especially to a resulting C6/C7 weight ratio of or below 1%:1%. Alternatively, also the ratio of molar concentrations may be decreased accordingly, e.g. preferably with a decrease to a molar ratio in the food product to a resulting C6/C7 molar ratio of or below 2000:1, preferably to a resulting C6/C7 molar ratio of or below 100:1, more preferred to a resulting C6/C7 molar ratio of or below 10:1, especially to a resulting C6/C7 ratio of or below 1:1 (it has to be pointed out the ratio of % values is identical to the ratio of the values, i.e. 2000%:1%=2000:1).

Accordingly, new food products are provided with the present invention by use of this method. For example, a new generation of soft drinks or orange and apple juices are provided with the present invention that have a resulting C6/C7 molar ratio of or below 2000:1. Other preferred embodiments of food products according to the present invention have a C6/C7 weight or molar ratio of or below 3000:1, especially of or below 2500:1; for example beverages that are derived from soft drinks (i.e. essentially without any sedoheptulose content) containing fruit juices, such as orange or apple juices, e.g. in an amount of 5 to 50%. Accordingly, the present invention also relates to a soft drink with a ratio of C6-carbohydrates to C7-carbohydrates (in % w/w: % w/w, % w/v: % w/v or as molar ratio) with a C6/C7 weight or molar ratio of or below 3000:1, preferably of or below 2500:1.

Virtually any food product (the term "food product" encompasses any ingestible material that can be nutritially used by humans, including food, beverages, etc.) can be improved according to the present invention by the addition of sedoheptulose. Preferably, the food product is selected from the group consisting of a nutritional drink, a nutritional snack bar, a diet food product, a cereal food product, a soft drink, a sports drink, energy drink, nutritional sweetener, candy, pastry, milk product, spreads or functional food product including instant meals.

According to another aspect, the present invention also relates to the improved food products as such that are provided with the present invention. As already stated, virtually any food product available on the market can be improved according to the present invention. The present invention provides novel products that have a sedoheptulose content or, if the available product already contains a certain level of sedoheptulose, have an increased sedoheptulose content. Accordingly, the present invention also relates to a food product with added sedoheptulose, wherein the sedoheptulose content is increased compared to the food product without added sedoheptulose by at least 10% w/w, preferably at least 20% w/w, especially at least 30% w/w. Preferably, the sedoheptulose content is increased compared to the food product without added sedoheptulose by at least 50% w/w, preferably at least 100% w/w, especially at least 200% w/w. These figures can—in addition—be also applied to liquid food products, such as beverages, in % w/v ratios (i.e. e.g. beverages wherein the sedoheptulose content is increased compared to the food product without added sedoheptulose by at least 50% w/v, preferably at least 100% w/v, especially at least 200% w/v).

If the food product available in the prior art is originally free of sedoheptulose, according to the present invention sedoheptulose can be added to provide a sedoheptulose content of the food product that is at least 0.001% w/w or % w/v, preferably to obtain a sedoheptulose content of the food product that is at least 0.01% w/w or % w/v, more preferred at least 0.1% w/w or % w/v, even more preferred at least 1% w/w or % w/v, especially at least 10% w/w or % w/v. Of course, the sedoheptulose content can even be much higher, depending on the nature of the food product (candies, etc.).

Preferably, the food product according to the present invention is selected from the group consisting of a nutritional drink, a nutritional snack bar, a diet food product, a cereal food product, a soft drink, a sports drink, energy drink, nutritional sweetener, candy, pastry, milk product, spreads or functional food product.

According to another aspect, the present invention provides a method for establishing for a food product a ratio of C6-carbohydrates to C7-carbohydrates (in % w/w, % w/v or molar concentration) by analysing the food product with respect to its content of C6-carbohydrates, especially glucose and fructose, and with respect to its content of C7-carbohydrates, calculating the ratio of the content of C6-carbohydrates to the content of C7-carbohydrates (in % w/w: % w/w, % w/v: % w/v or molar concentration ratio) for this food product, and, preferably recording this ratio on a data carrier or printing the ratio on a printing base and combining the data carrier or the printing base with the food product.

According to a variant of this aspect, the present invention also provides a method for establishing for and adjusting in a food product a ratio of C6-carbohydrates to C7-carbohydrates (in % w/w, % w/v or molar concentration) by analysing the food product with respect to its content of C6-carbohydrates, especially glucose, fructose and sucrose and maltose as respective dimers, and with respect to its content of C7-carbohydrates, calculating the ratio of the content of C6-carbohydrates to the content of C7-carbohydrates (in % w/w: % w/w, % w/v: % w/v or molar concentration ratio) for this food product; then adding sedoheptulose to the food product in an amount that the ratio of the content of C6-carbohydrates to the content of C7-carbohydrates (in % w/w: % w/w, % w/v: % w/v or molar concentration ratio) for this food product is decreased by at least 10%, preferably at least 50%, especially at least 100%; and, preferably, recording this ratio on a data carrier or printing the ratio on a printing base and combining the data carrier or the printing base with the food product. As already stated above, preferably, the weight or molecular ratio in the food product is decreased to a resulting C6/C7 ratio of at least 2000%:1%, preferably to a resulting C6/C7 ratio of at least 10%:1%, especially to a resulting C6/C7 ratio of at least 1%:1%.

BRIEF DESCRIPTION OF THE DRAWINGS

The present invention is further described in the following examples and the figures, yet without being restricted thereto.

FIGS. 1A-1D: (A) Pooled samples from carrots or leaves of indoor grown Sedum Spectabile plants were analyzed by gas-chromatography coupled to mass spectrometry to specifically measure relative glucose (C6) and sedoheptulose (C7) levels. The ratio of C6/C7 was calculated by dividing their respective peak area. (B) Sedoheptulose and glucose levels were further assessed by GC-MS in serum of individuals before and after food uptake to investigate if diet-derived C7 can enter the human blood-stream. Sedoheptulose and glucose level of four overnight fasted (fasted) individuals (empty bars) were compared to levels measured two hours after a meal (diet-fed, grey bars) containing mainly carrots (~700 g) with some olive-oil, salt and pepper. The change in serum carbohydrate levels was expressed as mean fold change (n=4,+/− S.D.). (C) Concentrations of glucose, fructose and sedoheptulose were measured in the carbohydrate-extracts of indicated beverages. Mean values of four pooled technical replicates were blotted to demonstrate extracted sugar concentrations. Furthermore (D), the C6/C7 (sedoheptulose) ratio was established by dividing the sum of glucose and fructose (C6) molecules or weight by respective sedoheptulose (C7) unit (N.A.=not applicable).

FIGS. 3A-3N: (A-E) Primary human adipocytes were obtained by differentiation of the stromal vascular cell fraction in the presence of glucose and fructose (GF, 1.5 g/L of each sugar; total carbohydrates 3 g/L) or sedoheptulose supplemented media, which was termed GFS (1 g/L of each sugar; total carbohydrates 3 g/L), for eight days. Subsequently mRNA levels of (A) CARKL, (B) adiponectin and (C) uncoupling protein 1 (UCP-1) was assessed by RT-PCR and compared between the groups. (D) Cellular oxygen consumption rates (OCR) and (E) extracellular acidification rates (ECAR) of adipocytes were recorded in the presence of indicated carbohydrate-mix (mean+/−S.D., n=9-11). (F) Tumor necrosis factor alpha (TNFa) and (G) interleukin 6 (IL-6) mRNA expression levels of mature murine adipocytes cultivated for three days in cell culture media containing either GF or GFS carbohydrate mix, or (H) IL-6 expression in primary murine hepatocytes, as well as (I) TNFa and (J) IL-6 mRNA levels in primary bone marrow derived macrophages, both cell types were pre-cultured for two days in GF or GFS media, were compared between respective groups. Secretion of (K) TNFa and (L) IL-6 cytokines over the period of two days was measured by ELISA in the supernatant of bone marrow derived macrophages. LPS-induced (100 ng/ml) secretion of (M) TNFa 2 hrs after activation and (N) IL-6 6 hrs after activation in the respective media by macrophages was also measured by ELISA. Data represents mean+/−S.D., n=3)

FIGS. 6A-6G: (A) The immune system of sedoheptulose kinase overexpressing mice (CARKL) and control littermates was challenged with a sub-lethal lipopolysaccharide injection (LPS, 7 mg/kg) and a panel of 19 cytokines was measured 24 hrs after immune activation in serum. Data represents relative mean fluorescence intensities (MFI) of individual cytokines measured in wild type (WT=100%) and CARKL serum by milliplex map mouse cytokine profiler (n=3,+/− SD). Monocyte chemoattractant protein-1 (MCP-1) and TNFa mRNA expression of murine mature adipocytes isolated from (B and C) subcutaneous or (D and E) epididymal white adipose tissue of WT and CARKL mice. Data represent mean values, n=3,+/− SD. (F) Incidence of stroke and rs465563 genotype. Data were compared by Pearson's $\chi^2$-tests. ** . . . p<0.01. (G) Duration of initial stroke-free survival was assessed by Kaplan-Meier plots. Individuals homozygous for the rs465563: [G]-allele show significantly shorter event-free times than carriers of the [A]-allele.

EXAMPLES

Figure 2A:
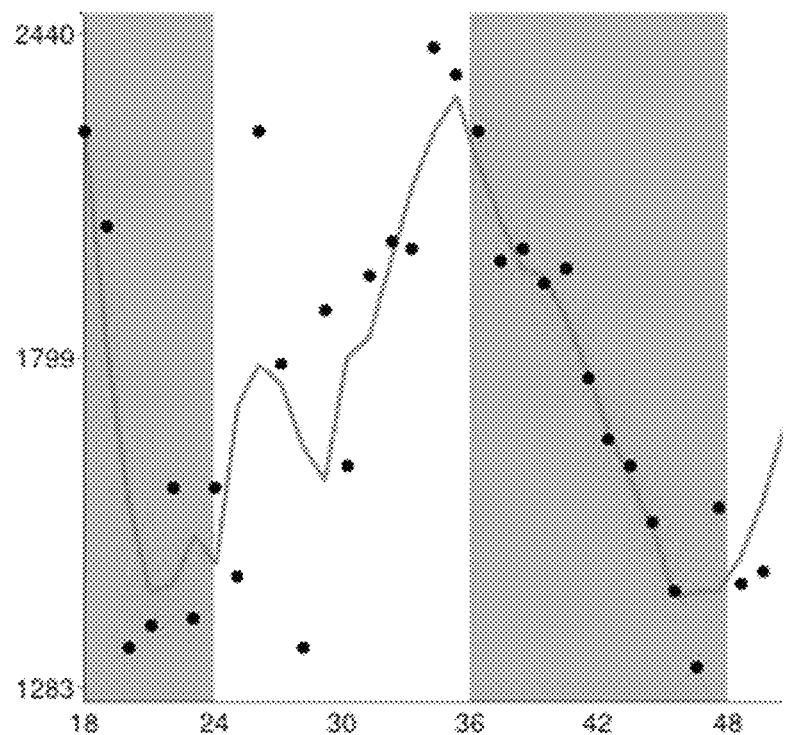
FIGS. 2A-2D: (A) Blot of normalized sedoheptulose kinase (CARKL) mRNA expression levels in mouse liver over a period of 48 hrs was obtained from the public available "Circadian Gene Expression Database—CIRCA". Y-axis represents normalized gene expression and X-axis time in hours. (B and C) Reduced and oxidized nicotinamide adenine dinucleotide levels of cells with perturbed CARKL expression were calculated from previously recorded metabolomics data (Haschemi et al., 15 (2012), 813-826). RAW264.7 cell line either (B) expressing high CARKL levels by overexpression or (C) low CARKL levels by shRNAmir expression were compared to individual control cell lines to illustrate CARKL mediated nicotinamide adenine dinucleotide regulation. Data represent mean fold change of three individual experiments+/− SEM. (D) CARKL mRNA levels were measured in a mouse cDNA tissue library. Data represents normalized (to β-actin) mean CARKL expression relative to thymus CARKL expression in fold change (all tissues n=3, S.D.).

Materials and Methods
Carbohydrates

Glucose and fructose were purchased from Sigma Aldrich. Sedoheptulose was isolated from the plant *sedum Spectabile* or *sedum telephium* (Haschemi et al., Cell Metab. 15 (2012), 813-826) and was further purified by chromatography.
Glucose and Sedoheptulose Measurements in Carrots and Human Serum Fresh carrots with an Austrian "organic-certificate" were sliced into small pieces and snap-frozen in liquid nitrogen. The same procedure was applied to leaves freshly harvested from indoor-grown *Sedum Spectabile* plants. Three samples of each tissue were pooled and homogenized to powder by glass-beads. The carbohydrate rich fractions of the samples were isolated by 20% $H_2O$ and 80% MeOH extraction solution spiked with 13C standards and processed for standard gas-chromatography coupled to mass spectrometry (GC-MS). Glucose and sedoheptulose were identified by their individual masses and their relative amount was derived from the peak area of each individual analyte normalized to 13C content. Glucose and sedoheptulose were also measured in equal volumes of serum from overnight fasted or carrot fed individuals. The carrots were steamed and some olive-oil, salt and pepper were used for flavour. Two hours before and two hours after the carrot containing meal human serum was prepared in VACUETTE® Z Serum Sep tubes from blood. Serum samples were processed as previously described and also analyzed by GC-MS as detailed above and in Ruiz-Matute A I et al., Chromatogr B Analyt Technol Biomed Life Sci. 2011 May 15 879(17-18).
Glucose, Fructose and Sedoheptulose Concentration in Beverages Indicated beverages were purchased from a local grocery store and were all pre-packed. From each beverage 1 ml (for each of four technical replicates) was aliquoted and vaccuum concentrated on a SpeedVac. This was followed by MeOH/H2O (80:20) precipitation and a centrifugation step to clear the carbohydrate fraction in the supernatant from precipitate. Each supernatant was again lyophilized in a SpeedVac, rehydrated in equal volumes of water and technical replicates were pooled. For carbohydrate analysis a Dionex ICS-3000 DC metal-free system was used with a CarboPac PA1 column (250×4 mm) and a CarboPac PA1 guard column (both from Dionex) at a flow rate of 1 mL min-1. Elution was carried out isocratically with 16 mM NaOH for the first 20 min. Then a linear gradient to 100 mM NaOH was applied from 20 to 40 min followed by an increase over two minutes to 200 mM hold until 47 min. The starting condition with 16 mM NaOH was reached again at 49 min and kept until 70 min. Parameters of the pulsed amperometric detection are exactly as recommended in the Technical Note 21 (Optimal Settings for Pulsed Amperometric Detection of Carbohydrates Using the Dionex ED40 Electrochemical Detector) from Dionex. Chromatograms were evaluated according to chromatograms of authentic glucose, fructose and sedoheptulose standards, each 100 µM.
Human Adipocyte Culture Stromal vascular fraction cells (SVFs) from subcutanous white adipose tissue of a patient undergoing abdominal surgery were isolated as described before (Lindroos et al, Cell Metab. 2013 Jul. 2; 18(1):62-74.). Briefly, adipose tissue was digested with Collagenase II (Worthington) and filtered. SVFs were separated from mature adipocytes by centrifugation, followed by the lysis of erythrocytes in the SVF-fraction (Buffer EL, Qiagen). The purified SVFs were cultured in DMEM/F12, 10% FBS (Gibco, Life Technologies). As soon as the cells reached confluence, they were washed with DMEM/F12 w/o glucose (Biowest) and the medium was replaced by DMEM/F12 with a total carbohydrate load of 3 g/L, containing 1.5 g/L glucose and fructose or 1 g/L each of glucose, fructose, and sedoheptulose, respectively. Two days after confluence (day 0), differentiation was induced by adding 1 µM dexamethasone, 1.74 µM insulin, 5 µM troglitazone, 0.5 µM IBMX, 17 µM pantothenic acid and 33 µM biotin. After two days, IBMX and dexamethasone were omitted, while insulin and troglitazone were removed on day 4. 50% of the medium was replaced on day 6. Two days later, the cells were harvested for RNA isolation (RNeasy mini kit, Qiagen).
Mature Murine Adipocytes Ceiling Culture Anterior and posterior subcutaneous adipose tissue and epididymal white adipose tissue was isolated from transgenic CARKL-mice and wild-type littermate controls. Adipose tissue was digested as described above for the human sample. After centrifugation, the layer of floating mature adipocytes was removed and re-centrifuged at 100 rcf for 10 minutes. 150 µL of packed adipocytes were cultured under a floating coverslip in six-well plates, in DMEM/F12, 15% calf serum (PAA). 24 hours after isolation, the wells were washed twice with PBS and the medium was exchanged to DMEM/F12 with a total carbohydrate load of 3 g/L, containing 1.5 g/L glucose and fructose, or 1 g/L each of glucose, fructose and sedoheptulose, respectively. Three days later, the cells were harvested for RNA isolation using TRIreagent (Sigma).
Hepatocyte Culture Hepatocytes were isolated from male wild-type and CARKL overexpressing mice after the mice were sacrificed by hepatic in situ collagenase perfusion. After perfusion, the liver was quickly removed, minced, and filtered through a cell strainer (Fisher Scientific, Inc) into a 50 ml sterile tube. Hepatocytes in the resulting filtrate were purified from the nonparenchymal cells by centrifugation steps. The isolated hepatocytes were seeded into plates at a concentration of 0.25×10^6/ml in respective DMEM-media containing 10% FBS and indicated carbohydrate mixes at 3 g/L (glucose and fructose (GF), or glucose, fructose and sedoheptulose (GFS)) at least two days before experiments were performed.

Bone Marrow Derived Macrophages and Osteoclasts Culture

Mouse bones were isolated from male wild-type and CARKL overexpressing mice and bone marrow wash flushed, washed and cleared from redblood cells by lysis, and subsequently differentiated in DMEM containing 25 mM glucose and 20 ng/ml M-CSF. After 4 days, cells for osteoclast differentiation were harvested and seeded in corning osteo assay plates with differentiation media (see below), and for primary bone marrow derived macrophages (BMDM) the medium was renewed and further supplemented with M-SCF for two days. Differentiated BMDM were then seeded in respective DMEM-media containing 10% FBS and indicated carbohydrate mixes at 3 g/L (glucose and fructose (GF), or glucose, fructose and sedoheptulose (GFS)) at least two days before experiments were performed.

In Vitro Bone Resorption Assay

Osteoclast precursor cells (bone marrow cells treated with 20 ng/ml M-CSF for 4 days) were plated in 24-well Corning Osteo Assay plate in the presence of 10 ng/ml M-CSF and 100 ng/ml RANKL in alpha-MEM medium containing 10% FBS and 3 g/L either glucose and fructose (GF), or glucose, fructose, and sedoheptulose (GFS). The Medium was renewed every third day. After 7 days, cells were removed with bleach and washed three times with water before Von Kossa staining according to standard protocols from Corning (technical review) was performed to enhance contrast between the intact assay surface and resorption pit. Each well was entirely photographed by TissueFax with an ×20 objective and all visible resorption pits were counted and analysed blinded.

Extracellular Acidification Rates and Oxygen Consumption Rates

The XF-Analyzer (Seahorse Bio.) was used to measure changes in cellular metabolism induced by different carbohydrates. Extracellular acidification rates (ECAR, mpH/min) and oxygen consumption rates (OCR, pmoles/min) were recorded in primary human adipocytes and primary murine hepatocytes according to the manufacture instructions. Briefly, cells were seeded in seahorse cell plates at a density of $10^4$ cells per well for adipocytes and $0.5 \times 10^5$ cells per well for hepatocytes. At the day of experiments the cells were washed with carbohydrate free media and incubated for one hour in indicated media containing carbohydrate mixes at a concentration of 3 g/L (glucose and fructose (GF), or glucose, fructose and sedoheptulose (GFS)). To measure glucose-induced ECAR, cells were starved for one hour in carbon free media before glucose (1 g/L) was added to the well per automatic injection. Glucose-induced ECAR was normalized to respective ECAR before glucose addition (basal=100%). Changes induced by the different carbohydrate sources were expressed as relative change in % to illustrate the effect of each carbon source.

Gene Expression Analysis

Briefly, total RNA was extracted and reverse-transcribed using commercial kits (QIAGEN, Applied Biosystems). Quantitative real-time PCRs were performed on an Abi-PRISM 7900HT real-time cycler using iTaq SYBR Green Supermix with ROX (BioRad) to measure CARKL, adiponectin, UCP-1, TNFa, IL-6, MCP-1, and beta-actin expression as previously described (Haschemi et al., Cell Metab. 15 (2012), 813-826). Expression of target gene was normalized to beta-actin expression. Relative expression of target gene was calculated by the delta-delta CT method.

Sedoheptulose Kinase Assay

The ADP Quest Assay (DiscoveRx) was used to indirectly measure S7P formation by ADP accumulation over time according to the manufacture instructions. Recombinant sedoheptulose kinase was previously produced in E.coli and purified by affinity purification (Haschemi et al., Cell Metab. 15 (2012), 813-826).

Indirect Calorimetry

The respiratory quotient (VCO2 production/VO2 consumption) and energy expenditure (EE, kcal/day/kg^0.75) per activity of mice were measured in metabolic cages (Harvard Apperatus) by indirect calorimetry. Either one CARKL transgenic mouse or a wild-type littermate, was housed per cage for one day before it was started to record mean respiratory quotient and energy expenditure per activity during day (8 am to 4 pm) and night (8 pm to 4 am).

Insulin Tolerance Test

Four hours pre-starved female CARKL-transgenic mice and wild type littermate controls were i.p. injected with 0.75 U insulin/kg body weight. Blood glucose was measured before the injection and 15, 30, 45 and 60 minutes after injection by using one-touch glucose strips (Accu Check, Roche).

Oil Red Staining

Briefly, hepatocytes were cultured as indicated before the medium was removed and cells were fixed by 10% formalin. After a wash with 60% isopropanol the wells were incubated with Oil Red O solution (Sigma-Aldrich) and stained for 10 min, washed 4 times with water before photographs were taken at ×20 magnification.

Glucose-6-Phosphate Dehydrogenase Activity Assay

Cells were grown on polystyrene vessel tissue culture treated glass slides, snap frozen in liquid nitrogen and kept at −80° C. The enzyme histochemical procedure was based on the tetrazolium salt method as described by Van Noorden and Frederiks. The incubation medium for the demonstration of G6PD activity contained 18% (w/v) polyvinyl alcohol (average molecular weight 70,000-100,000) in 0.1 M Tris-Maleate buffer, pH 7.5, 15 mM glucose-6-phosphate, 0.8 mM NADP, 0.4 mM magnesium chloride, 0.45 mM 1-methoxyphenazine methosulphate, 5 mM sodium azide and 5 mM tetranitroblue tetrazolium chloride. The medium was freshly prepared immediately before incubation. Control reactions additionally contained 40 mM glucosamine-6-phosphate. Cells were incubated at room temperature for 15 minutes under continuous mixing by orbital shaker. After incubation, cells were washed 3×5 minutes in 60° C. phosphate buffered saline, dried, and mounted in glycerol gelatin, and photographed within one day at ×10 magnification.

Immune Challenge and Cytokine Response Profiling In Vivo

For sublethal murine in vivo endotoxemia, 7 mg/kg LPS (Sigma Aldrich) were injected intraperitoneally in male CARKL transgenic or wild-type littermates. Serum was isolated by VACUETTE® mini Z Serum Sep tubes from whole blood. Cytokine were measured by milliplex map mouse cytokine profiler according to manufactures instructions (Millipore). All animal experiments were carried out according to an ethical animal license protocol and contract approved by the Medical University Vienna (BMWF-66.009/0140-II/10b/2010).

CARKL Single Nucleotide Polymorphism (SNP) Association-Study with Risk of Stroke.

Study Design: 578 neurologically asymptomatic patients from the Inflammation and Carotid Artery—Risk for Atherosclerosis Study (ICARAS, Schillinger et al., (2005) Circulation 111 (17):2203-2209.)), recruited until March 2003, were included into the present analysis—inclusion and exclusion criteria have been published previously. Briefly, asymptomatic carotid artery disease, representing the primary inclusion criterion, was defined as the absence of transient ischemic attacks (TIA), amaurosis fugax and stroke within the last 12 months or of residual symptoms, respectively. Besides exhaustive medical examination (including anamnesis, physical status and blood testing), patients underwent sonography of the carotid arteries at baseline and at a follow-up 6-9 months after study inclusion as previously described (Schillinger et al., (2005) Circulation 111 (17): 2203-2209.). Incidence of cardiovascular events was recorded until January 2006. This analysis was approved by the local ethics committee (EC-No. 1933/2012) and has been performed in accordance with the ethical standards specified by the Declaration of Helsinki and its amendments.

Definitions: Arterial hypertension was defined as repetitive resting blood pressure above 140/90 mm Hg and was assumed to be present in patients with antihypertensive medication. Hyperlipidemia was diagnosed in patients with a total serum cholesterol >200 mg/dL or LDL cholesterol >130 mg/dL and was considered to be present in all patients taking lipid-lowering drugs. Diabetes mellitus was diagnosed as supposed by Expert Committee on the Diagnosis and Classification of Diabetes Mellitus. Peripheral artery disease was graded using Fontaine's classification system, coronary artery disease was defined according to the classification by the Canadian Cardiovascular Society (CCS). Anamnestic myocardial infarction was defined according to Alpert. Stroke was defined by a neurological deficit persisting >24 h and was evaluated according to the modified Rankin stroke scale. Progression of carotid artery atherosclerosis was defined as an increase in stenosis by at least one NASCET angiographic degree.

Genotyping: DNA was isolated from EDTA-anticoagulated whole blood by means of spin-column based nucleic acid purification. Genotyping was done on an ABI TaqMan® 7900HT fast-realtime thermocycler (Applied Biosystems, Rotkreuz, Switzerland) using the 5'-Nuclease-Assay [7]. This assay includes the sequence-specific binding of labeled DNA-probes. During the annealing phase of each step, sequence-specific probes containing a fluorophore on their 5'-ends bind their respective allele. The fluorescence of the fluorophore is masked by a 3'-quencher, until the 5'-Taq-polymerase separates these compounds by its 5'-exonuclease activity during the elongation phase. End-point-measurement of the intensity of sequence-specific fluorescence indicates the presence of the corresponding allele. In the present study, rs465563 was analyzed in a total reaction volume of 10 µL using a commercially available TaqMan® SNP genotyping assay (Assay ID: C_____ 717358_1_, Applied Biosystems) and TaqMan® Genotyping Master Mix (Applied Biosystems) according to the standard protocol supplied by the manufacturer. The results were interpreted using SDS 2.4 sequence detection software (Applied Biosystems).

Statistical Analysis: Continuous data are given with respect to its distribution as mean and standard deviation or median and interquartile range. Categorical data are presented as counts and percentage. Presence of normal distribution within subgroups was assessed by Kolmogorov-Smirnov-tests. Metric variables were compared by Mann-Whitney U tests. Connections between genotypes and study end points as well as relative risks were estimated by contingency-tables and Pearson's $\chi^2$-tests. Event-free survival was estimated by Kaplan-Meier-Analysis, data was compared pairwise by Log Rank (Mantel-Cox) tests. Multivariable models were calculated by means of binary logistic regression and evaluated by drawing ROC (Receiver-Operator-Characteristics) plots. Results were considered statistically significant at p<0.05 unless otherwise noted. All p-values were interpreted two-sided unless otherwise stated. All statistical calculations were done using IBM SPSS 20.0 (IBM Corporation, Armonk, USA).

Results

Diet-Derived Sedoheptulose Uptake in Humans

To determine if nutritional sedoheptulose is absorbed from diets via the digestive tract into the human blood, which is a critical step for sedoheptulose to become a metabolic active carbohydrate, glucose (C6) and sedoheptulose (C7) levels were measured in carrots and in human serum. To determine the C6/C7 ratio of carrots plant tissue was homogenized, extracted the small molecule fractions and measured simultaneously relative glucose and sedoheptulose amounts by GC-MS (FIG. 1A). Leaves of Sedum Spectabile, a succulent plant which contains high sedoheptulose levels, were analyzed in parallel as positive control. The leaves of Sedum Spectabile contained glucose and approximately twice as much sedoheptulose, which resulted in a C6/C7 ratio of approximately 0.5. In fresh food grade organic carrots almost equal quantities of glucose and sedoheptulose were detected and thereby a C6/C7 ratio of around 1. Potatoes, in contrast to carrots, were reported to contain no sedoheptulose (Kardon et al., FEBS Lett. 2008 Oct. 15, 582(23-24)) and are therefore expected to possess a very high (or even infinite) C6/C7 ratio. Next it was addressed if diet-derived sedoheptulose, originating from carrots, reaches the human blood by monitoring serum level of glucose and sedoheptulose before and after a meal containing mainly steamed carrots (~700 g per male adult) with some olive-oil, salt and pepper. Two hours after the meal, an approximately two-fold increase in sedoheptulose serum levels was observed in humans (FIG. 1B). This result clearly indicated that nutritional sedoheptulose is absorbed by the human digestive tract and that it enters the blood to become available as a carbohydrate for subsequent metabolism. Serum glucose levels normalized already within two hours after food uptake and thereby suggest that humans metabolize sedoheptulose and glucose differently.

These results indicate that carrots, which are considered as healthy vegetables and constituents of diets around the world, are a natural sedoheptulose source for humans. It is interesting to mention that carrots, although they contain carbohydrates such as glucose, are suitable and well tolerated by diabetics and even protect people with common genetic risk factors for type-2 diabetes (Patel C J et al., Hum Genet. 132 (2013): 495-508).

The C6/C7 Ratio in Natural and Manufactured Human Food Products

Next, the concentration of glucose, fructose and sedoheptulose was measured in carbohydrate extracts from Coca-Cola®, Red Bull®, orange-, apple-, tomato-, and carrot-juice to establish the C6/C7 index for common beverages and thereby estimate the actual human sedoheptulose-exposure. Soft- and energy drinks contained glucose and fructose but no sedoheptulose (FIG. 1C). Fruit-juices contained similar amounts of C6 (the sum of glucose and fructose) as soft-/energy drinks (100 mM range), but in contrast to the latter they also contained sedoheptulose in the 100 µM range. In vegetable-juices glucose and fructose levels were reduced, whereas sedoheptulose concentrations were found greatly increased (mM range). The C6/C7 ratios of the individual beverages, calculated as molar—as well as weight ratios, are given in FIG. 1D. In two fruit-juices C6/C7 ratios of around 2000/1 were found. In tomato- and carrot-juices the ratio was 75/1 and 20/1, respectively; Coca-Cola® and Red Bull® contained no detectable amounts of sedoheptulose. Hence, the C6/C7 ratio for these drinks could not be calculated and is therefore not applicable (N.A.) to such food products if they are not additionally supplemented with C7. These findings clearly indicate that manufactured food products lack carbohydrate complexity and therefore also sedoheptulose. Notably, in absolute numbers these data indicate that 1 kg of diet-derived sedoheptulose is consumed per 9 kg diet-derived glucose if the natural carbon-mixture of carrot-juice was chosen over soft-/energy drinks—the consequences of chronic sedoheptulose deprivation by an unbalanced human nutrition are currently unknown.

Sedoheptulose Kinase Oscillates and is Highly Expressed in Metabolically Active Tissue.

Figure 2B:
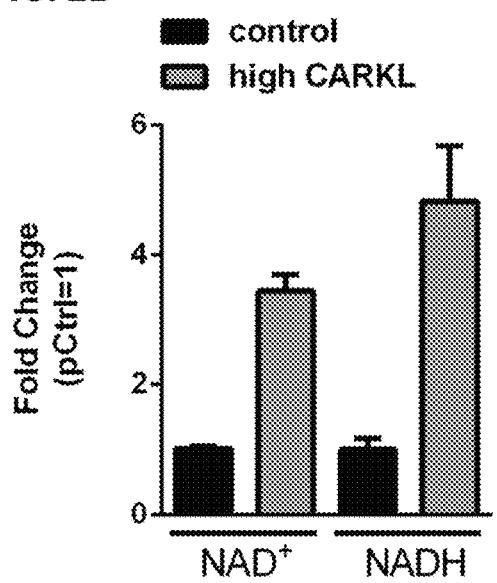
Figure 2C:
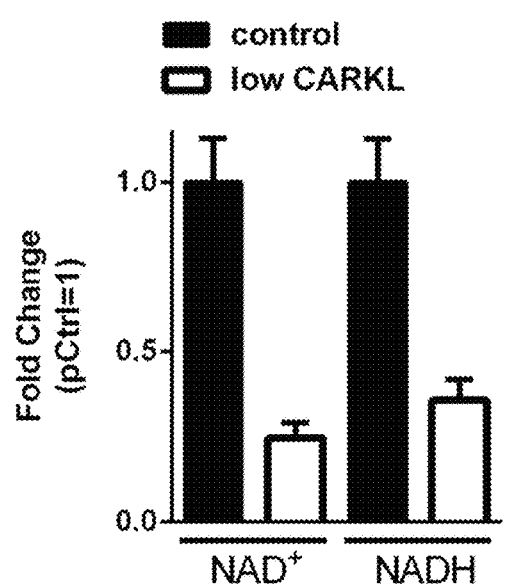
Figure 2D:
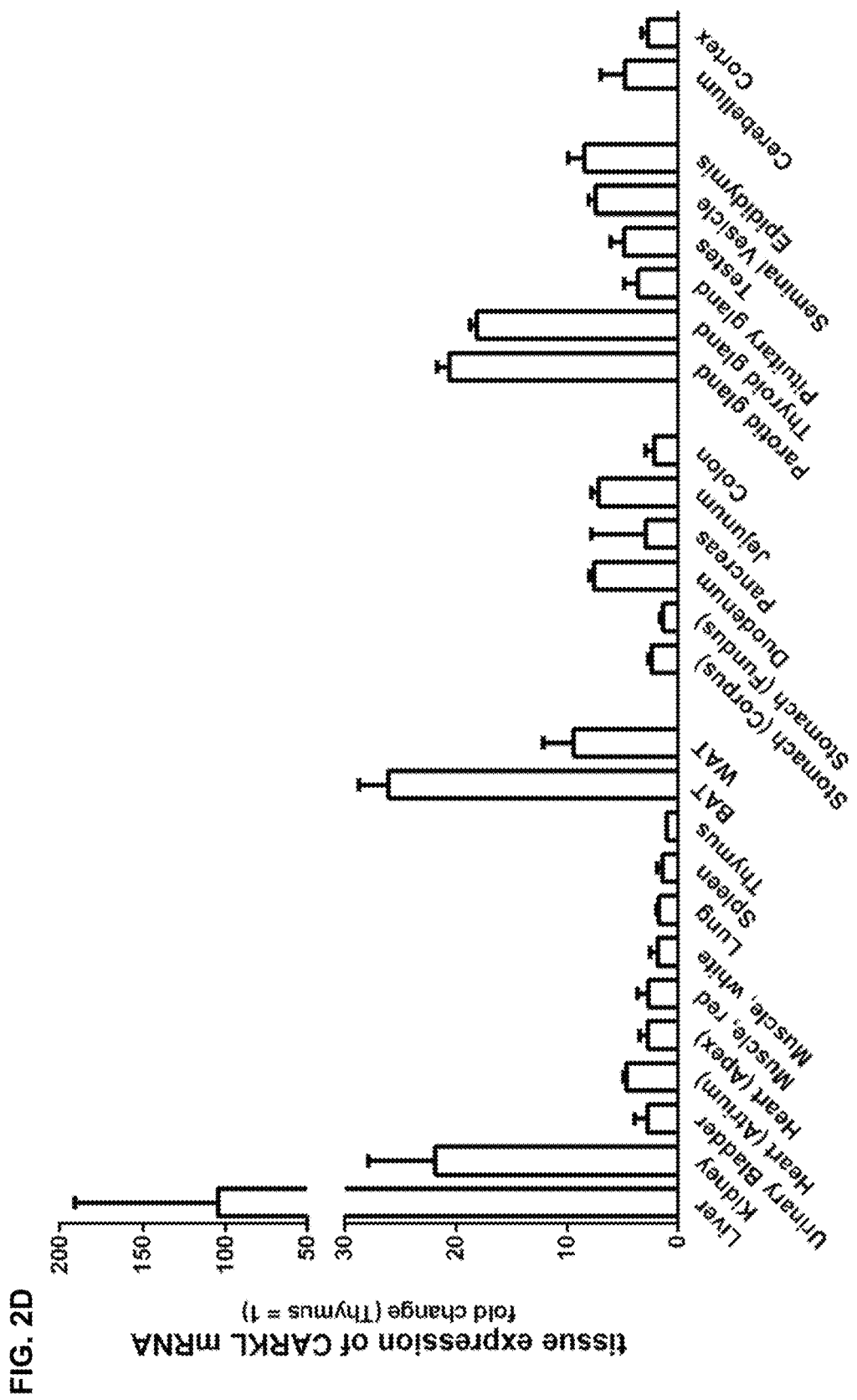

To understand how sedoheptulose kinase CARKL and therefore sedoheptulose metabolism is distributed and controlled in various mammalian tissues, different tissues were tested for mRNA expression levels. CARKL expression, in a publicly available database for circadian expression profiles (CircaDB), was found oscillating in mouse liver (period 20.0, FIG. 2A) and adrenal gland (period 24.0, data not shown). Sedoheptulose-7P levels were previously reported to oscillate in plants, peaking during the regenerative-phase of carbon-fixation to reconvert ribose moieties. The mammalian circadian clock is in part set by the redox-state. CARKL overexpressing RAW264.7 cells indicated that high sedoheptulose kinase expression induces a 4 fold increase of redox-factors like reduced nicotinamide, adenine dinucleotide (NADH) and also glutathione (GSH) level increase (FIG. 2B and Haschemi et al., Cell Metab. 15 (2012), 813-826). Deficiency of CARKL and therefore also lack of sedoheptulose turnover showed the opposite effect (FIG. 2C). This data indicates that sedoheptulose metabolism is under the control of circadian rhythm and acts simultaneously as modulator of cellular redox-states. In order to specify which tissue consumes nutritional sedoheptulose, mRNA levels of sedoheptulose kinase (CARKL) were measured in a mouse cDNA tissue library (FIG. 2D). Sedoheptulose kinase is the rate-limiting enzyme of sedoheptulose metabolism and was highly expressed in liver, kidney, in brown and white adipose tissue (BAT and WAT), digestive organs, in glands, in the male reproductive system as well as in the brain. These results demonstrate that diet-derived sedoheptulose can become a systemic carbohydrate source for many tissues but especially for metabolically active organs such as the liver, kidney and adipose tissue.

Sedoheptulose Metabolism is Important for the Function and Metabolic Health of Cells To investigate the metabolic consequences of exposure to sedoheptulose, human and murine cells in the culture media were exposed to either glucose in combination with fructose (GF) or to glucose, fructose and sedoheptulose (GFS), while keeping the total carbohydrate load constant. The function of adipocytes, hepatocytes and macrophages was tested to evaluate the importance of sedoheptulose in complementing nutritional carbohydrate loads. The sedoheptulose used in these experiments was isolated from *sedum telephium* plants.

In the human body, adipocytes fulfil the crucial function to store energy in form of lipids and are therefore very important cells to maintain health. In metabolically unhealthy or in most morbidly obese patients adipocytes do not function properly, increase their cell size to account for excessive lipid loads, become inflamed (meta-inflammation, a low-grade but chronic type of inflammation) and ultimately contribute to the development of disorders like insulin resistance or cardio-vascular diseases. In human adipocytes, differentiated from subcutaneous precursor cells, an increase in sedoheptulose kinase CARKL mRNA expression was found if sedoheptulose was added to the culture media (FIG. 3A). Furthermore, an increase in adiponectin and UCP-1 expression, two functional relevant adipocyte marker genes, was observed in the GFS compared to GF treated cells (FIGS. 3B and 3C). To test for changes in cellular metabolism, cellular oxygen consumption rates (OCR) and extracellular acidification rates (ECAR) were measured as indicators for mitochondrial respiration and lactic acid fermentation, respectively. Human adipocytes, differentiated and cultured in sedoheptulose containing media, showed comparable ECAR to WT controls, while their cellular oxygen consumption rates were increased (FIGS. 3D and 3E).

Together, these data show that subcutaneous adipocytes maintain and improve their function (increase in adiponectin, UCP-1 and oxygen consumption) in the presence of sedoheptulose compared to a situation where only glucose and fructose are present as bio-fuel.

To better define the beneficial role of sedoheptulose in preventing metabolically unhealthy states like chronic low-grade inflammation, the cytokine profiles of primary mature murine adipocytes, primary murine hepatocytes, and naïve as well as lipopolysaccharide (LPS)-induced activated primary macrophages cultured in GF or GFS media were measured. Mature adipocytes, which were cultivated in sedoheptulose containing media, produced less TNFa and IL-6 mRNA than adipocytes cultivated with glucose and fructose alone (FIGS. 3F and 3G). Similarly to that, hepatocytes also produced less IL-6 if cultivated with sedoheptulose (FIG. 3H). In primary macrophages basal TNFa and IL-6 mRNA expression, and cytokine secretion were found blocked by sedoheptulose containing media (FIG. 3I-L). LPS-induced macrophage activation resulted in strongly enhanced TNF-a and IL-6 secretion in GF cultured cells (FIGS. 3M and 3N). LPS-induced macrophages cultivated in GFS media increased IL-6 to comparable levels as GF treated macrophages, but reduced their TNFa secretion by approximately 40%. This shows that addition of sedoheptulose to macrophages on the one hand reduces their basal inflammatory state, measured by TNFa and IL-6, but on the other hand retains their natural function in immunity as seen for IL-6.

To conclude, addition of sedoheptulose to the culture media significantly enhanced subcutaneous adipocyte function and reduced the inflammatory state of cells and thereby might positively influence the pathogenesis of obesity, type II diabetes and cardiovascular diseases also summarized in part by the metabolic syndrome.

Sedoheptulose Kinase CARKL Overexpression

Figure 4A:
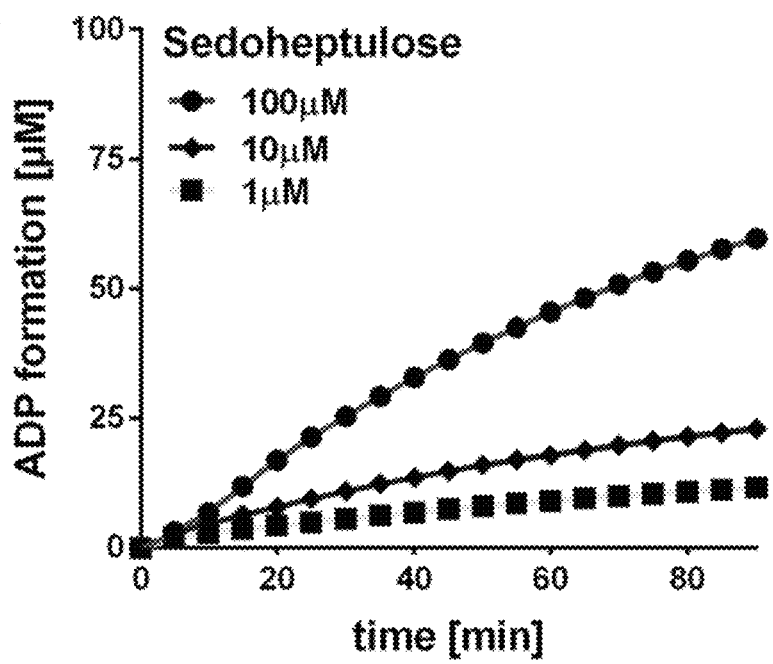
FIGS. 4A-4H: In an in vitro kinase assay, which employs ADP formation as activity readout, the sedoheptulose turnover rate at constant ATP (150 µM) concentration was enhanced either by (A) increasing sedoheptulose concentration or (B) by increasing the amount of the rate-limiting enzyme sedoheptulose kinase (CARKL). (C-E) Hepatocytes from wilt-type (WT) and sedoheptulose kinase CARKL overexpressing mice were pre-cultured for two days in GFS containing media before basal (C) ECAR and (D) OCR was recorded of these cells. (E) Hepatocytes from both genetic linages (CARKL and WT controls) were cultivated in GF or GFS containing media and then pre-starved (no-carbohydrates) for 1 h to measure glucose-induced ECAR after the addition of glucose to reach a final concentration of 1 g/L in the culture media mean+/−S.D., n=7-11). As metabolic in vivo indicators (F) the respiratory quotient (RQ) and (G) energy expenditure (EE, kcal/day/kg^0.75) per activity by indirect calorimetry were determined and compared CARKL to wild-type (WT) littermates during day (8 am to 4 pm) and night (8 pm to 4 am). Data represent mean values, n=3, +/− SD. (H) Insulin tolerance test in mice was performed on pre-starved (4 h) female CARKL-transgenic and wild type littermate controls by i.p. injection of 0.75 U insulin/kg body weight. Blood glucose was measured before the injection (control) and 15, 30, 45 and 60 minutes after injection and graphed as relative value in % of control. Data represent mean values+/−SD, n=3-4.
Figure 4B:
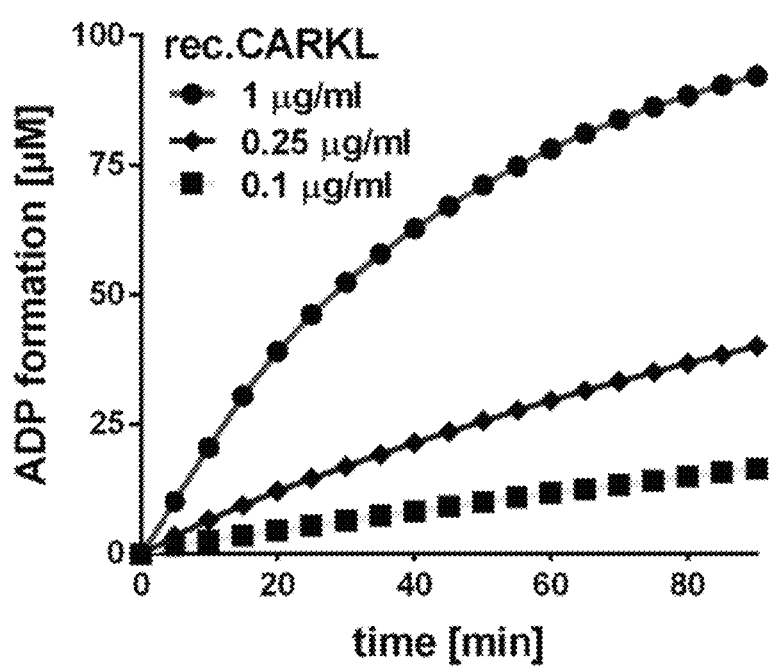

Transgenic mice overexpressing sedoheptulose kinase ubiquitously in the entire body were generated to isolate genetically engineered primary cells overexpressing CARKL and to test sedoheptulose metabolism in vivo. CARKL transgenic mice did not show any obvious phenotypes and their organ weight was not different to organ weights of WT littermate control animals (data not shown). It was hypothesized that increased sedoheptulose metabolism can either be achieved by increasing the concentration of the substrate sedoheptulose, or by elevating the level of its rate-limiting enzyme sedoheptulose kinase (CARKL). To test this in an in vitro kinase assay, a constant amount of recombinant CARKL protein was incubated with increased doses of sedoheptulose. This resulted in enhanced sedoheptulose turnover rates as measured by ADP formation (FIG. 4A). The same effect was observed by increasing CARKL protein concentration, while sedoheptulose concentration was kept constant (FIG. 4B). These results demonstrate that CARKL overexpression is a valid model to investigate the effects of increased sedoheptulose metabolism. Next, primary hepatocytes, as liver tissue appeared to endogenously metabolize sedoheptulose (FIG. 2D), were isolated to study the effects of C7- and C6-metabolism at increased CARKL expression levels.

Figure 4C:
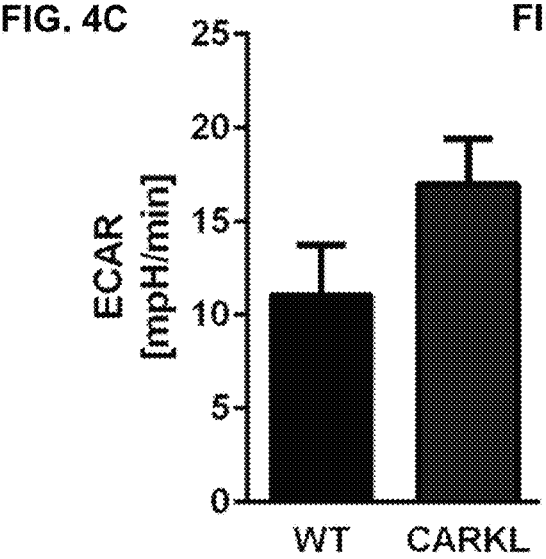
Figure 4D:
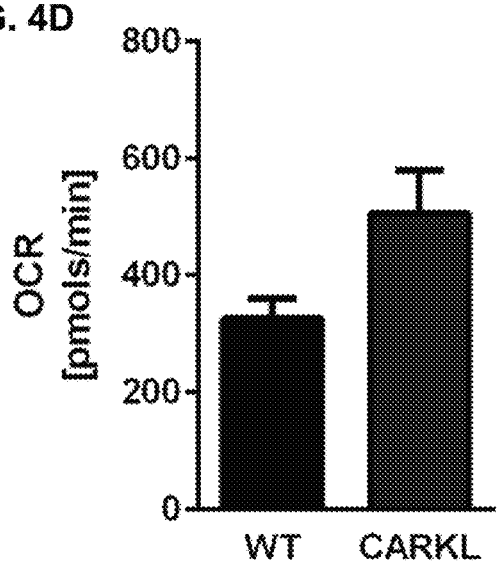
Figure 4E:
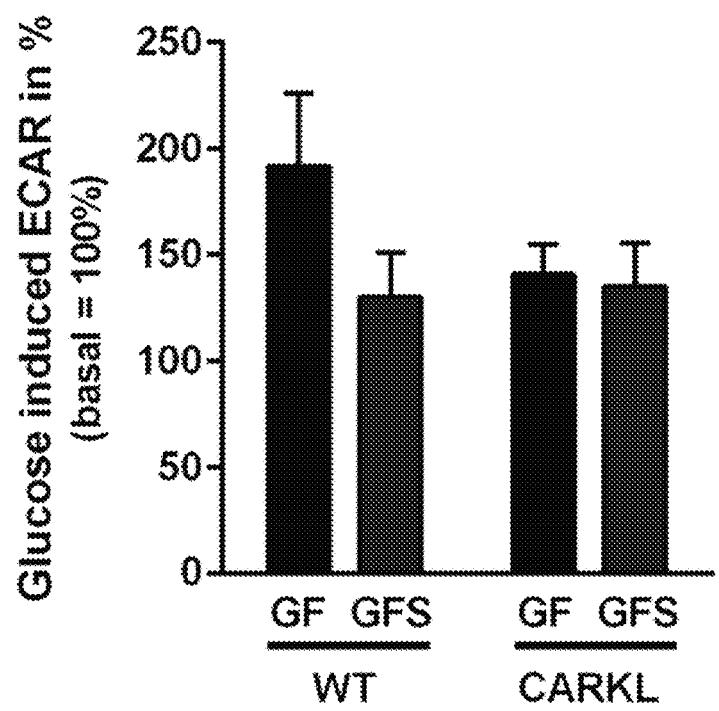

Hepatocytes were cultured in media with a C6/C7 sugar ratio of 2:1 and metabolically assessed by comparing the ECAR and OCR as more general metabolic-parameters. Hepatocytes from CARKL overexpressing mice significantly increased their metabolic rate as increased ECAR and OCR levels indicated if compared to WT control cells (FIGS. 4C and 4D). It appeared that sedoheptulose induced a more efficient metabolism in these cells. To test for the relevance of sedoheptulose and sedoheptulose kinase expression together, hepatocytes isolated from WT and CARKL mice were incubated in GF and GFS containing culture media and their glucose-induced ECAR was compared (after 1 hr carbohydrate starvation) as a measure to control cellular glycolysis. In WT hepatocytes glucose-induced ECAR was reduced by sedoheptulose administration (FIG. 4E). In line with this data, glucose-stimulated hepatocytes from WT animals cultured in GF (without sedoheptulose) routed a larger part of glucose to lactic acid fermentation, whereas cells from CARKL overexpressing mice appeared to balance the same glucose bolus more efficiently. These results further supported the previous data and clearly pointed out that increased sedoheptulose metabolism has distinct and beneficial effects on cells, which are important for metabolic health.

Sedoheptulose Metabolism In Vivo

Figure 4H:
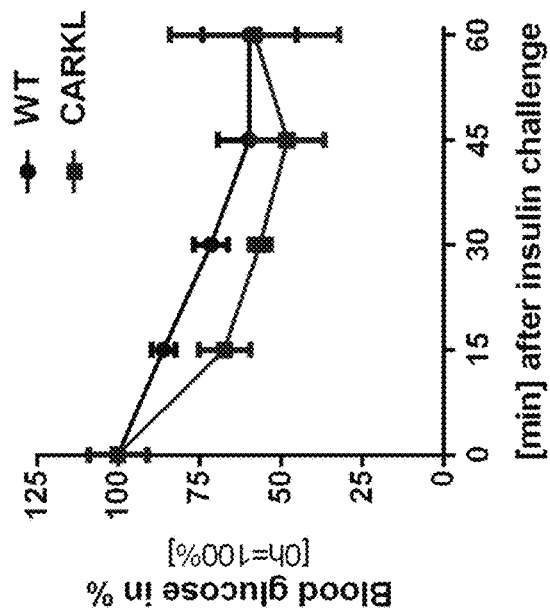
Figure 4F:
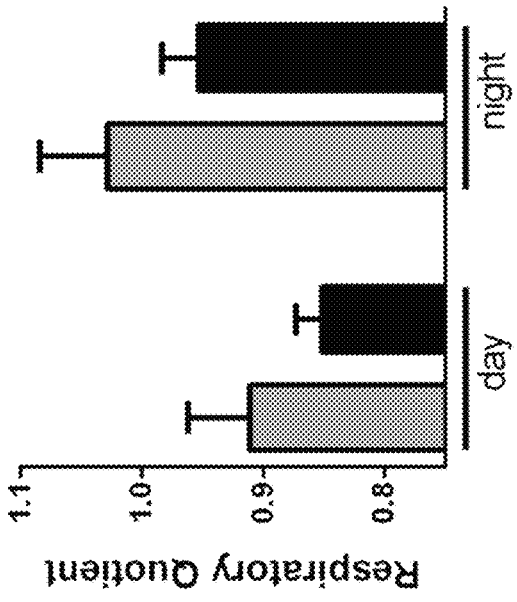
Figure 4G:
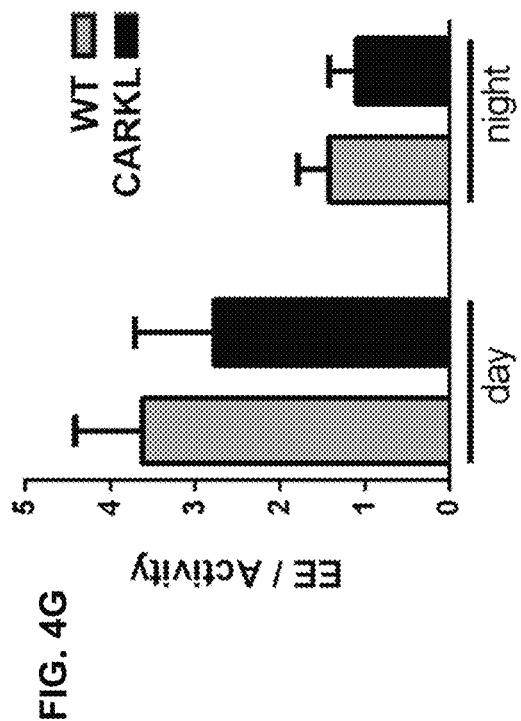

After validating cellular phenotypes of sedoheptulose kinase overexpression in hepatocytes the metabolic effect of increased sedoheptulose turnover to an entire organism was investigated by comparing the respiratory quotient (RQ; RQ=exhaled $CO_2$/oxygen consumption), as well as energy expenditure per physical activity of control and sedoheptulose kinase transgenic mice, measured by indirect calorimetry during day and night as systemic indicators of metabolism (FIGS. 4F and 4G). Sedoheptulose kinase overexpressing animals (CARKL) have lower RQ values compared to wild type (WT) littermates. CARKL mice showed increased oxygen consumption and therefore lower RQ values, and thereby partly mirrored the effects of sedoheptulose on cells. Furthermore, CARKL mice also tend to have a lower EE per activity if compared to control mice. The insulin sensitivity of female CARKL transgenic and WT mice were also compared by an insulin tolerance test (ITT), to investigate if sedoheptulose metabolism also affects insulin signalling in vivo. Insulin injection (i.p.) lowered the blood glucose level in mice overexpressing sedoheptulose kinase faster than in WT controls, indicating that insulin sensitivity was also increased in these animals by increasing sedoheptulose metabolism (FIG. 4H). In this context it is important to mention that induction of insulin resistance in mature adipocytes, by TNFa and hypoxia treatment, resulted in sedoheptulose kinase loss (public Gene expression omnibus data available at http://www.ncbi.nlm.nih.gov/geo/query/acc.cgi?acc=GSM1261655).

Together, these experiments showed that increased sedoheptulose metabolism does not only alter metabolism in vitro but also in vivo. The lower RQ values observed in CARKL mice combined with the by trend lower EE per physical activity and the increased insulin sensitivity are indicative for a more efficient and sustainable metabolic program, which can be induced by increasing sedoheptulose metabolism.

Hepatic Lipid Deposition is Reduced by CARKL

Figure 5A:
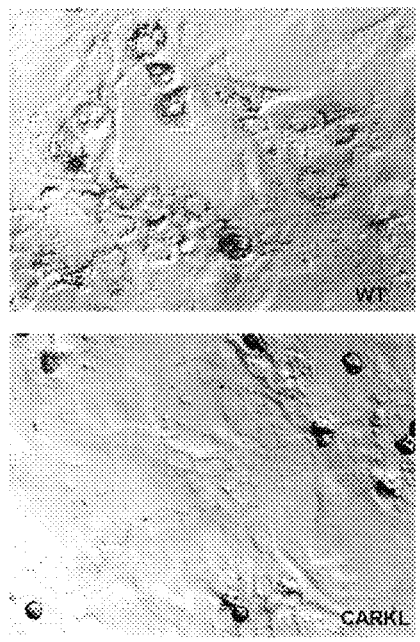
FIGS. 5A-5D: (A) Lipid deposition in hepatocytes isolated from either WT or CARKL overexpressing mice and cultivated in control medium (GF) was visualized by oil red staining. Representative micrographs were acquired with a 20× objective. (B) Glucose-6-phosphate dehydrogenase activity was measured in hepatocytes isolated from either WT or CARKL overexpressing mice and cultivated in control medium (GF) for two days. Arrows indicate re-localization of G6PD activity. Representative micrographs were acquired with a 10× objective. (C and D) Osteoclasts from WT or CARKL overexpressing mice were differentiated and cultivated for 7 days in Corning Osteo Assay plates in GF or GFS containing media. Their resorption-activity was assessed by counting all pits per well which were visible at 20× magnification. Data represent mean values, n=2-3,+/− SD. (D) Two representative images of the largest resorption-pits found in WT osteoclast either cultured in GF or GFS containing media are shown. Micrographs were acquired by 40× magnification.

Extensive lipid deposition in hepatocytes results in fatty liver disease and can be accompanied by inflammation (i.e. non-alcoholic steatohepatitis (NASH)) causing liver fibrosis, cirrhosis, and eventually hepatocellular carcinoma. The lipid content of hepatocytes from WT and CARKL overexpressing mice was compared and it was found that hepatocytes from CARKL mice contained less lipid droplets than their WT controls (FIG. 5A).

In conclusion, high liver fat content, especially in combination with inflammation, including malfunction of adipocytes, increases risk of many diseases including type 2 diabetes or cancer, thus both, the reduction of inflammation and lipid accumulation in hepatocytes by sedoheptulose might be especially valuable for human nutrition (see vegetables, which contain high C7 levels).

CARKL Regulates Glucose-6-Phosphate Dehydrogenase Activity.

Figure 5B:
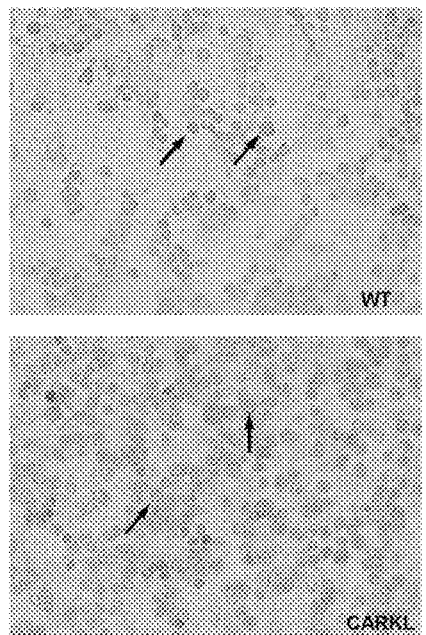

Glucose-6-phosphate dehydrogenase (G6PD), the rate limiting enzyme of the oxidative arm of the pentose phosphate pathway (PPP) which generates C5 bodies i.e. for nucleotide synthesis and redox-equivalents, was previously shown to be directly inhibited by p53 (tumor-suppressor) (Jiang et al., Nat Cell Biol. 2011 Mar. 13 (3):310-6). Mutation in p53, the most frequently mutated gene in human tumors, results in hyper-activation of G6PD and lipid accumulation in hepatocytes. Sedoheptulose kinase is the rate-limiting kinase of the non-oxidative arm of the PPP and was previously shown to reduce the oxidative PPP-flux, at least in macrophages. To test for a possible regulation of G6PD activity in hepatocytes by sedoheptulose metabolism, the enzyme activity of WT and CARKL overexpressing cells was compared (FIG. 5B). In WT control cells G6PD activity was observed to be evenly distributed, whereas in cells from CARKL mice a re-localization of G6PD and thereby a reduced activity in the inner space of the cells was observed. Interestingly, the same phenotype was achieved by incubating WT cells in cell culture media with sedoheptulose (not shown). If re-localization and/or inhibition of G6PD by sedoheptulose kinase overexpression and sedoheptulose incubation were the cause for the reduced lipid accumulation in hepatocytes (FIG. 4A) remains to be established. Nevertheless, this data in combination with data from macrophages shows that an elevated sedoheptulose level may act as a countermeasure for p53 loss in cancer cells, at least by negatively regulating G6PD activity in some instances. Another example are estrogen dependent breast cancer cells which decrease CARKL expression in response to growth factor estrogen (public GeneChip repository data available at http://www.ncbi.nlm.nih.gov/geoprofiles/; ID: 53372898; GDS3285/219713_at/SHPK), which in turn might again result in increased G6PD activity and subsequently tumor growth.

This data also implements sedoheptulose metabolism as a suitable target to regulate G6DP activity and for future anti-cancer strategies.

Sedoheptulose and Bone Metabolism

Bone is an extremely dynamic tissue. The fine balance of bone formation and resorption is essential for the proper mechanical stability of bone. Disequilibrium between bone formation and resorption is the cause of osteoporosis, a highly prevalent condition of reduced bone density and disturbed bone micro-architecture resulting in bone fragility and pathological fractures. As the osteoclasts, the cells responsible for bone resorption are derived from the monocyte lineage, whose function is strongly impacted by sedoheptulose metabolism, it was also tested whether osteoclast function may be modulated by the C6/C7 ratio.

Figure 5C:
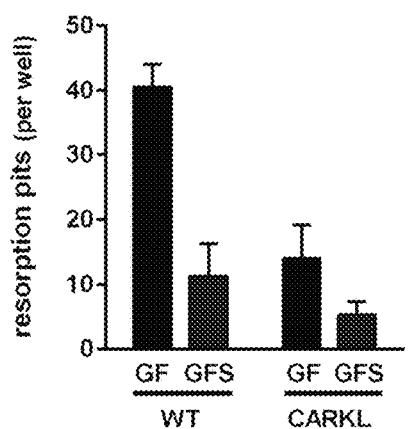
Figure 5D:
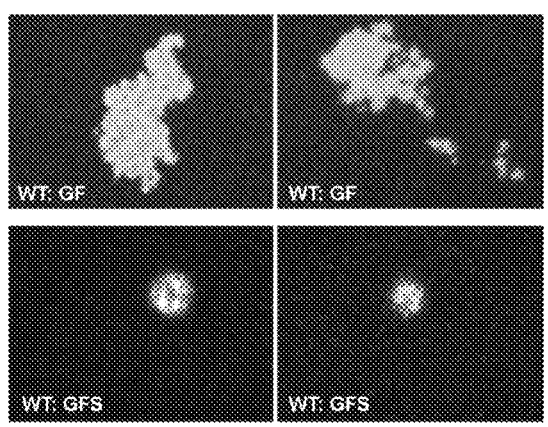

Bone marrow cells were differentiated in vitro to osteoclasts by exposing the cells to M-CSF in combination with RANKL. The cells were cultured in plates, pre-coated with a bone mineral matrix at the bottom of the well, to provide substrate for their bone-resorption activity. Analysis of the substrate resorption clearly demonstrated that both, CARKL overexpression as well as increasing C7 content in the culture media, reduced pit formation by osteoclasts (FIG. 5C). Interestingly, larger resorption-pits were found only in the absence of sedoheptulose (FIG. 5D).

Again, this data supports the concept of the present invention that a well-balanced C6/C7 ratio is crucial to maintain health and that C7 has the potential to alleviate the pathophysiologic situations of i.e. osteoporosis in humans.
Sedoheptulose Kinase Regulates the Immune Response of Animals Data of CARKL overexpression and its effects on the mouse immune-system in a model of acute immune activation and in low-grade inflammation of mature adipose tissue is presented with the present examples. In CARKL mice acute-inflammation was elicited by a sub-lethal lipopolysaccharide (LPS) injection, which resulted in a suppressed cytokine response compared to wild-type controls (FIG. 6A). A panel of 19 cytokines was measured in WT and CARKL mouse serum, which was isolated 24 hrs after LPS injection (7 mg/kg, IP), by mouse cytokine profiler. Twelve cytokines reached the threshold of 50% mean change, which was defined as cut-off to highlight cytokines regulated by CARKL overexpression in vivo. IL-13, MIP1α, RNATES, IL-12 (p'70), IL-2, TNF-α, MCP1, KC, GM-CSF, IL-6, IL-17 and IL-15 were decreased by at least 50% mean change in CARKL mice compared to wild-type littermates. Cytokines IL-6, IL-17 and IL-15 even reached a threshold of 75% mean change. In addition to acute-inflammation, the basal levels of pro-inflammatory cytokines in mature adipose tissue were also assessed from two different depots (subcutaneous and epididymal adipose tissue) of CARKL and WT control mice. Consistently with the reduction in LPS-induced inflammation, mRNA levels of TNFa and MCP1, a primary adipokine which recruits macrophages to adipose tissue and which belongs to the pro-inflammatory cytokines, were found blunted by CARKL overexpression (FIG. 6B-E).

This indicates that a nutritional supplement containing sedoheptulose might dampen acute and low-grade chronic inflammation. Therefore, targeting C7 metabolism, either by nutritional or clinically applied sedoheptulose appears as an effective measure to reduce inflammation and associated disorders.
A Single Nucleotide Polymorphism (SNP) in the 3'-UTR of the CARKL Gene is Associated with the Risk of Stroke.

Figure 6F:
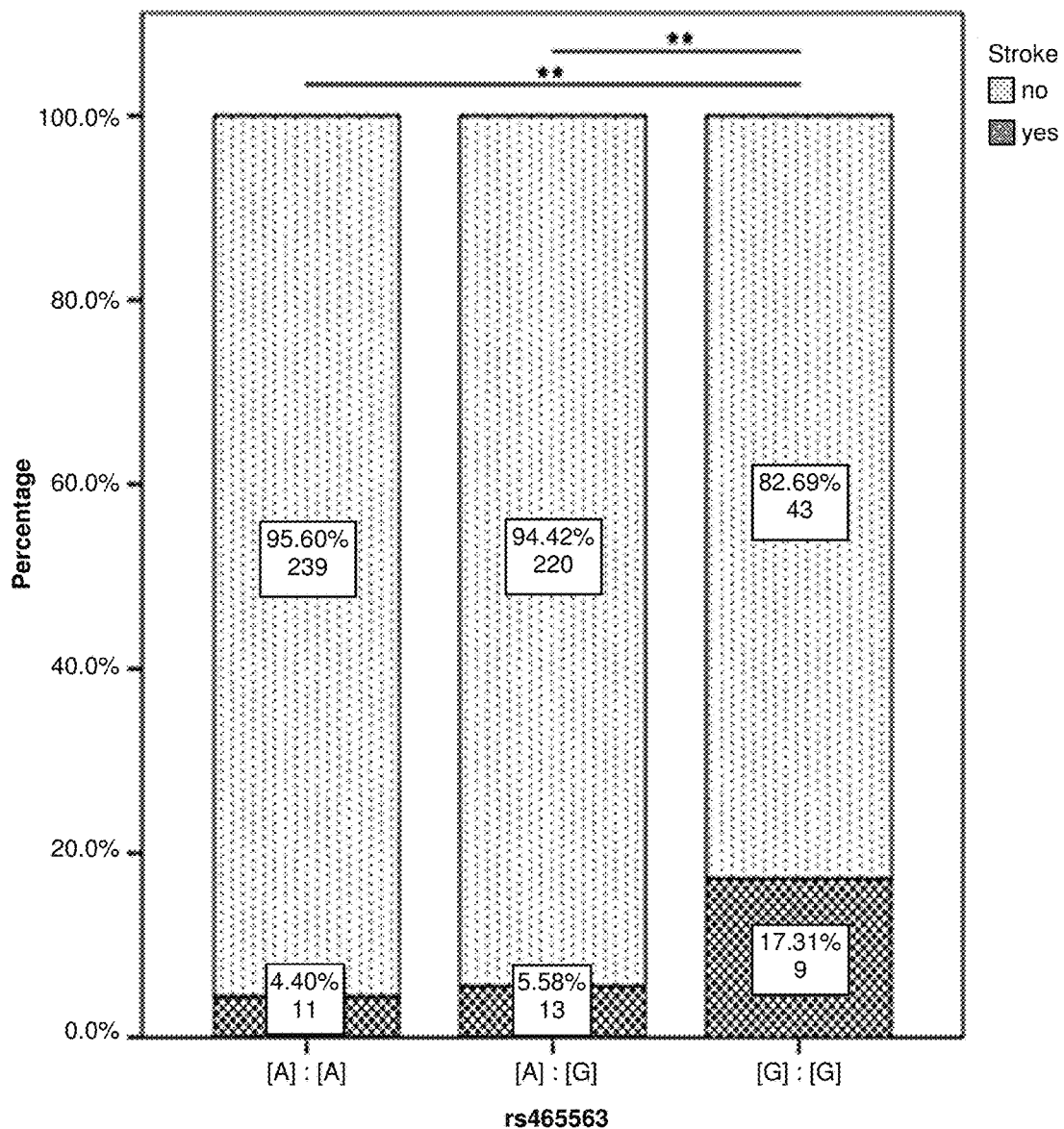

535 neurologically asymptomatic patients from the Inflammation and Carotid Artery—Risk for Atherosclerosis Study (ICARAS, Schillinger et al., (2005) Circulation 111 (17):2203-2209) were genotyped for the rs465563 [A] to [G] substitution in the 3'-UTR of the CARKL gene. 33 (6.2%) patients suffered a stroke within the observation period. In those patients, the distribution of rs465563 alleles was significantly different compared to the allele frequencies of the rest of the study population ($\chi^2=12.639$, df=2, p=0.002, see FIG. 6F). In detail, homozygous carriers of the [G]-allele bore a relative risk of 3.93 (95% CI: 1.72-9.01) compared to [A]-homozygous, and 3.10 (95% CI: 1.40-6.87) compared to heterozygous individuals, respectively. Statistical independence of rs465563 genotype information was assessed by a binary logistic regression model providing age, sex, histories of myocardial infarction and stroke, nicotine consumption, body mass index, as well as certain comorbidities (hyperlipidemia, hypertension, diabetes mellitus) as covariates (model: $\chi^2=30.476$, df=11, p=0.001). Within this model, carrier status of the [G]; [G] genotype presented as significant predictor (odds ratio=5.015, 95% CI: 1.803-13.943) when compared to patients homozygous for the [A]-allele. Moreover, it has been assessed by drawing Kaplan-Meier plots whether initial stroke-free survival time depends on rs465563 carrier status. Indeed, homozygous carriers of the [G]-allele (1518,3 days, 95% CI: 1419,2-1617,4) presented with significantly shorter event-free survival than heterozygous individuals (1619.1 days, 95% CI: 1584.8-1653.3, p=0.005) and carriers of the [A]; [A]-genotype (1788.1 days, 95% CI: 1755.7-1820.4, p=4.9.10-4) (FIG. 6G). Individuals homozygous for the rs465563: [G]-allele show significantly shorter event-free times than carriers of the [A]-allele.

The mechanistical background of this clinical association remains to be clarified. However, given the ability of CARKL to modulate macrophage polarization and the key role of the latter in the formation and progression of atherosclerotic plaques, it seems likely that the rs465563 polymorphism may impact on the risk of cerebrovascular events via modulation of macrophage polarization within atherosclerotic plaques. This notion is supported by the observation according to the present invention that the 3'-UTR of the CARKL gene is mainly transcribed in macrophages.

In conclusion, this association and the provided data on metabolism and function of adipocytes, hepatocytes, and macrophages in combination with reduced inflammation and enhanced insulin sensitivity in vitro and in vivo strongly indicates that sedoheptulose (C7-sugar) is a critical constituent for human nutrition and simultaneously a highly relevant medication to treat i.e. C7-defiencies or other metabolic unhealthy disease states.

The invention claimed is:
1. A method comprising:
obtaining a nutritional supplement comprising sedoheptulose; and
administering said nutritional supplement to a subject, wherein the nutritional supplement is administered with or has been added to a food product and wherein the sedoheptulose of a food product has been analysed with respect to its content in % w/w, % w/v, or molar concentration of C6-carbohydrate and with respect to its content in % w/w, % w/v, or molar concentration of C7-carbohydrate to establish a ratio of C6-carbohydrates to C7-carbohydrates in % w/w:% w/w %, w/v:% w/v, or as a molar ratio for this food product and the nutritional supplement is adminstered with or has been added to the food product in an amount to decrease the ratio of C6-carbohydrates to C7-carbohydrates in a combination of the food product and the nutritional supplement by at least 50%.
2. The method of claim 1, wherein the nutritional supplement is administered with or has been added to the food product in an amount to decrease the ratio of C6-carbohydrates to C7-carbohydrates in the combination of the food product and the nutritional supplement by at least 100%.
3. The method of claim 1, wherein the sedheptulose induces cellular oxygen consumption in the subject.

4. The method of claim 1, wherein the sedheptulose inhibits extracellular acidification, glycolysis, and lactate formation in the subject.

5. The method of claim 1, wherein the sedheptulose reduces glycaemic load in a food product consumed by the subject.

6. The method of claim 5, wherein the nutritional supplement is administered with or has been added to a food product already containing sedoheptulose to obtain a sedoheptulose concentration supplied to the subject that is increased at least 10% relative to a sedoheptulose content of the food product in an absence of the nutritional supplement.

7. The method of claim 5, wherein the food product is a liquid.

8. The method of claim 1, wherein the nutritional supplement can treat a sedoheptulose deficiency in a healthy individual.

9. The method of claim 8, wherein the nutritional supplement is administered with or has been added to a food product already containing sedoheptulose to obtain a sedoheptulose concentration supplied to the subject that is increased at least 100% relative to a sedoheptulose content of the food product in an absence of the nutritional supplement.

10. The method of claim 1, wherein the nutritional supplement is administered with or has been added to a food product.

11. The method of claim 10, wherein the nutritional supplement is with or added to the food product to obtain a sedoheptulose content of the food product that is at least 0.1% w/w.

* * * * *